United States Patent
Dessen et al.

(10) Patent No.: US 11,385,174 B2
(45) Date of Patent: Jul. 12, 2022

(54) METHOD FOR THE QUALITATIVE AND QUANTITATIVE DETECTION OF ALGINATE OLIGOMERS IN BODY FLUIDS

(71) Applicant: AlgiPharma AS, Sandvika (NO)

(72) Inventors: Arne Dessen, Røyken (NO); Philip Rye, Eiksmarka (NO); Paul Lewis, West Glamorgan (GB)

(73) Assignee: ALGIPHARMA AS, Sandvika (NO)

(*) Notice: Subject to any disclaimer, the term of this patent is extended or adjusted under 35 U.S.C. 154(b) by 0 days.

(21) Appl. No.: 17/264,559

(22) PCT Filed: Jul. 30, 2019

(86) PCT No.: PCT/EP2019/070511
§ 371 (c)(1),
(2) Date: Jan. 29, 2021

(87) PCT Pub. No.: WO2020/025617
PCT Pub. Date: Feb. 6, 2020

(65) Prior Publication Data
US 2022/0074853 A1    Mar. 10, 2022

(30) Foreign Application Priority Data
Jul. 31, 2018  (GB) .................................. 1812473

(51) Int. Cl.
*G01N 21/35* (2014.01)
*G01N 21/3577* (2014.01)
*G01N 33/487* (2006.01)

(52) U.S. Cl.
CPC ....... *G01N 21/3577* (2013.01); *G01N 33/487* (2013.01); *G01N 2021/3595* (2013.01); *G01N 2800/382* (2013.01)

(58) Field of Classification Search
CPC ............ G01N 21/3577; G01N 33/487; G01N 2021/3595
See application file for complete search history.

(56) References Cited

U.S. PATENT DOCUMENTS

2011/0229580 A1    9/2011   Srivastava et al.

FOREIGN PATENT DOCUMENTS

| WO | WO 2007/039754 A1 | 4/2007 |
| WO | WO 2007/039760 A2 | 4/2007 |
| WO | WO 2008/125828 A2 | 10/2008 |

(Continued)

OTHER PUBLICATIONS

Powell et al. "Targeted disruption of the extracellular polymeric network of Pseudomonas aeruginosa biofilms by alginate oligosaccharides, npj Biofilms and Microbiomes" (2018) 4:13 ; doi:10.1038/s41522-018-0056-3, Revised: May 20, 2018 Accepted: Jun. 6, 2018 (Year: 2018).*

(Continued)

*Primary Examiner* — Hugh Maupin
(74) *Attorney, Agent, or Firm* — Knobbe, Martens, Olson & Bear, LLP

(57) ABSTRACT

Qualitative and quantitative methods are for the detection of alginate oligomers in body fluids based on analyzing the Fourier transform infrared spectroscopy (FTIR) spectrum of a body fluid sample, for example a sputum sample, at a specific wave number range and, more particularly, certain specific characteristic wavenumbers.

21 Claims, 10 Drawing Sheets

(56) References Cited

FOREIGN PATENT DOCUMENTS

| WO | WO 2009/068841 A2 | 6/2009 |
|---|---|---|
| WO | WO 2010/139957 A1 | 12/2010 |
| WO | WO 2015/128495 A1 | 9/2015 |
| WO | WO 2018/146275 A1 | 8/2018 |

OTHER PUBLICATIONS

Lewis, PD, et al, 2010, "Evaluation of FTIR Spectroscopy as a diagnostic tool for lung cancer using sputum", BMC Cancer, 10:640.

Lewis, A.T., et al, 2013, "Detection of Lewis antigen structural change by FTIR spectroscopy", Carbohydrate Polymers 92, 1294-1301.

Lewis, P., et al, 2013, "Prediction of glycoprotein secondary structure using ATR-FTIR", Vibrational Spectroscopy 69, 21-29.

Menzies, G., et al, 2014, "Fourier transform infrared for noninvasive optical diagnosis of oral, oropharyngeal, and laryngeal cancer", Translational Research, 163:19-26.

Whiteman, S. C., et al, 2008, "FTIR spectroscopic analysis of sputum: Preliminary findings on a potential novel diagnostic marker for COPD", Therapeutic Advances in Respiratory Disease, 2(1) 23-31.

International Search Report in PCT/EP2019/070511, dated Oct. 24, 2019.

IPO Search Report, Application No. GB1812473.5, dated Jan. 25, 2019.

Boyd, Simon and Kirkwood, Jonah., "Quantitative analysis using ATR-FTIR Spectroscopy," Agilent.com [online], Available on the World-Wide-Web at: agilent.com/cs/library/applications/si-1374.pdftAccessed Jan. 21, 2019.

Nivens, David E., et al., "Role of Alginate and Its O Acetylation in Formation of *Pseudomonas aeruginosa* Microcolonies and Biofilms," Journal of Bacteriology, Feb. 2001, p. 1047-1057.

Powell, Lydia C., et al., "Targeted disruption of the extracellular polymeric network of *Pseudomonas aeruginosa* biofilms by alginate oligosaccharides," npj Biofilms and Microbiomes (2018).

Pritchard, Manon F., et al., "A New Class of Safe Oligosaccharide Polymer Therapy to Modify the Mucus Barrier of Chronic Respiratory Disease," Molecular Pharmaceutics, Mar. 7, 2016, vol. 13, No. 3, pp. 863-872.

\* cited by examiner

US 11,385,174 B2

METHOD FOR THE QUALITATIVE AND QUANTITATIVE DETECTION OF ALGINATE OLIGOMERS IN BODY FLUIDS

The present invention relates to methods for the detection of alginate oligomers in body fluids. Both qualitative and quantitative methods are provided. Alginate oligomers have been proposed as therapeutic agents and the methods of the invention may be used to monitor the distribution and/or the amounts of such agents in the body of the subjects to which they are administered, e.g. to determine, monitor and assess dosage regimes and/or the pharmacokinetics of alginate oligomer therapeutics. The methods of the present invention are based on analysing the Fourier transform infrared spectroscopy (FTIR) spectrum of a body fluid sample, e.g. a sputum sample, at a specific wave number range and, more particularly, certain specific characteristic wavenumbers.

Alginates are naturally occurring polysaccharides that have been found to have a number of uses, both clinical (e.g. in wound dressings, as drug carriers and in anti-heartburn preparations) and non-clinical (e.g. in food preparation). They are linear polymers of (1-4) linked β-D-mannuronic acid (M) and/or its C-5 epimer α-L-guluronic acid (G). The primary structure of alginates can vary greatly. The M and G residues can be organised as homopolymeric blocks of contiguous M or G residues, as blocks of alternating M and G residues and single M or G residues can be found interspacing these block structures. An alginate molecule can comprise some or all of these structures and such structures might not be uniformly distributed throughout the polymer. In the extreme, there exists a homopolymer of guluronic acid (polyguluronate) or a homopolymer of mannuronic acid (polymannuronate).

Alginates are typically isolated from natural sources such as marine brown algae (e.g. certain species of *Durvillea*, *Lessonia* and *Laminaria*) and bacteria such as *Pseudomonas aeruginosa* and *Azotobacter vinelandii* as large high molecular weight polymers (e.g. an average molecular weight in the range 300,000 to 500,000 Daltons). It is known, however, that such large alginate polymers may be degraded, or broken down, e.g. by chemical or enzymatic hydrolysis to produce alginate structures of lower molecular weight, e.g. less 35,000 Daltons. It is alginate molecules in this size range (referred to herein and in the art as alginate oligomers) that have been proposed for use in the treatment of CF and other respiratory diseases (see WO 2007/039754, WO 2008/125828 and WO 2015/128495) or to combat biofilm (WO 2009/068841) and multidrug resistant bacteria (WO 2010/139957).

Such applications for alginate oligomers create a need for methods for monitoring the amounts and distribution of alginate oligomers in the body of the subjects to which they are administered. Such techniques are useful in determining effective and safe dosage regimes for individual subjects and monitoring such treatment plans over the course of the subject's treatment. Such techniques are also useful in the analysis of the pharmacokinetics of alginate oligomers and thus have research applications.

We have now found that alginate oligomers have a distinct and reproducible infrared (IR) spectrum that surprisingly may be used to not only determine the presence or absence thereof in the complex molecular environments that are body fluids, e.g. sputum, with accuracy and sensitivity, but also to determine the concentration of the alginate oligomers in such fluids, with accuracy and sensitivity. More specifically, we have found that alginate oligomers have a characteristic and readily detectable IR absorbance or transmittance spectrum, in particular, in the wavenumber range 1200 $cm^{-1}$ to 900 $cm^{-1}$, and that such spectra, and IR absorbance or transmittance values at 1601±5 $cm^{-1}$, 1412±5 $cm^{-1}$, 1125±5 $cm^{-1}$, 1086±5 $cm^{-1}$, 1028±5 $cm^{-1}$, and 948±5 $cm^{-1}$ specifically, may offer particularly useful information, e.g. information on the concentration of alginate oligomer in the body fluid sample.

As a first aspect the invention therefore provides a method for determining the presence or absence of an alginate oligomer in a sample of body fluid, said method comprising:

(i) obtaining an infrared (IR) spectrum for the sample of body fluid, wherein the IR spectrum for the sample of body fluid is the second derivative of an IR absorbance spectrum from the wavenumber range of about 1200 $cm^{-1}$ to about 900 $cm^{-1}$ or the second derivative of an IR transmittance spectrum from the wavenumber range of about 1200 $cm^{-1}$ to about 900 $cm^{-1}$, (ii) providing an IR spectrum for the alginate oligomer, wherein the IR spectrum for the alginate oligomer is the second derivative of an IR absorbance spectrum from the wavenumber range of about 1200 $cm^{-1}$ to about 900 $cm^{-1}$ when the IR spectrum for the sample of body fluid is an absorbance spectrum, or a second derivative IR transmittance spectrum from the wavenumber range of about 1200 $cm^{-1}$ to about 900 $cm^{-1}$ when the IR spectrum for the sample of body fluid is a transmittance spectrum, and (iii) comparing the IR spectrum for the sample of body fluid to the IR spectrum for the alginate oligomer, wherein (a) an IR spectrum for the sample of body fluid which corresponds to the IR spectrum for the alginate oligomer is an indication that the alginate oligomer is present in the sample of body fluid, and (b) an IR spectrum for the sample of body fluid which does not correspond to the IR spectrum for the alginate oligomer is an indication that the alginate oligomer is absent from the sample of body fluid.

It will be appreciated immediately by the skilled person that steps (i) and (ii) may be performed in any order or simultaneously.

An IR absorbance or IR transmittance spectrum is a series of readings of IR absorbance or IR transmittance at a plurality of wavenumbers. In accordance with the invention the plurality of readings is taken from about wavenumber 1200 $cm^{-1}$ to about wavenumber 900 $cm^{-1}$, e.g. 1200±20 $cm^{-1}$, ±15 $cm^{-1}$, ±10 $cm^{-1}$, or ±5 $cm^{-1}$, to 900±20 $cm^{-1}$, ±15 $cm^{-1}$, ±10 $cm^{-1}$, or ±5 $cm^{-1}$, more particularly from wavenumber 1220 $cm^{-1}$, 1219 $cm^{-1}$, 1218 $cm^{-1}$, 1217 $cm^{-1}$, 1216 $cm^{-1}$, 1215 $cm^{-1}$, 1214 $cm^{-1}$, 1213 $cm^{-1}$, 1212 $cm^{-1}$, 1211 $cm^{-1}$, 1210 $cm^{-1}$, 1209 $cm^{-1}$, 1208 $cm^{-1}$, 1207 $cm^{-1}$, 1206 $cm^{-1}$, 1205 $cm^{-1}$, 1204 $cm^{-1}$, 1203 $cm^{-1}$, 1201 $cm^{-1}$, 1200 $cm^{-1}$, 1199 $cm^{-1}$, 1198 $cm^{-1}$, 1197 $cm^{-1}$, 1196 $cm^{-1}$, 1195 $cm^{-1}$, 1194 $cm^{-1}$, 1193 $cm^{-1}$, 1192 $cm^{-1}$, 1191 $cm^{-1}$, 1190 $cm^{-1}$, 1189 $cm^{-1}$, 1188 $cm^{-1}$, 1187 $cm^{-1}$, 1186 $cm^{-1}$, 1185 $cm^{-1}$, 1184 $cm^{-1}$, 1183 $cm^{-1}$, 1182 $cm^{-1}$, 1181 $cm^{-1}$, or 1180 $cm^{-1}$ to wavenumber 920 $cm^{-1}$, 919 $cm^{-1}$, 918 $cm^{-1}$, 917 $cm^{-1}$, 916 $cm^{-1}$, 915 $cm^{-1}$, 914 $cm^{-1}$, 913 $cm^{-1}$, 912 $cm^{-1}$, 911 $cm^{-1}$, 910 $cm^{-1}$, 909 $cm^{-1}$, 908 $cm^{-1}$, 907 $cm^{-1}$, 906 $cm^{-1}$, 905 $cm^{-1}$, 904 $cm^{-1}$, 903 $cm^{-1}$, 902 $cm^{-1}$, 901 $cm^{-1}$, 900 $cm^{-1}$, 899 $cm^{-1}$, 898 $cm^{-1}$, 897 $cm^{-1}$, 896 $cm^{-1}$, 895 $cm^{-1}$, 894 $cm^{-1}$, 893 $cm^{-1}$, 892 $cm^{-1}$, 891 $cm^{-1}$, 890 $cm^{-1}$, 889 $cm^{-1}$, 888 $cm^{-1}$, 887 $cm^{-1}$, 886 $cm^{-1}$, 885 $cm^{-1}$, 884 $cm^{-1}$, 883 $cm^{-1}$, 882 $cm^{-1}$, 881 $cm^{-1}$, or 880 $cm^{-1}$. Any ranges derived from these various range endpoints are specifically contemplated.

In accordance with the invention the plurality of IR absorbance or IR transmittance readings making up the spectrum are sufficient in number to permit a meaningful correlation analysis as described herein. The readings may be made at discrete wavenumbers or at discrete points between wavenumbers or may be a continuous reading across a plurality of wavenumbers, or a combination of both. The spectrum may be discontinuous and readings may be taken at wavenumbers or at points between wavenumbers which are not evenly spaced. The spectrum may be provided as portions from within the wavenumber range of the invention. Such portions need not be evenly spaced. In other embodiments the spectrum may be provided as a wider spectrum, in which case the relevant information is obtained by focusing on the wavenumber ranges of the invention. In certain embodiments the range of wavenumbers selected includes a region of the spectrum which may permit effective baseline correction calculations.

The second derivative of an IR spectrum is a specific mathematical decomposition of the basic IR absorbance/transmittance data and would be familiar to the skilled person and routine to perform. In brief, derivative spectra are obtained by calculating the rate of change across a defined region, or window, of wavenumbers within a spectrum. This window moves across the spectrum in a step-wise fashion. The Savitzky-Golay algorithm is used to define the parameters of derivative spectrum calculation. Different orders of derivative spectra can be calculated, depending on the application. Second order derivative spectra are calculated to increase the resolution of smaller peaks which make up broad peaks. Typically derivative spectra, including second derivative, are calculated from spectra obtained directly from the instrument used to prepare the spectra, i.e. spectra which have not undergone any substantive processing beyond routine background correction. In other embodiments second derivative may be calculated from IR absorbance/transmittance spectra which have undergone a pre-smoothing operation, e.g. using the Savitzky-Golay algorithm set to a derivative order 0.

Comparing the IR spectrum for the sample of body fluid to the IR spectrum for the alginate oligomer and assessing correspondence between the two may be a qualitative, semi-quantitative or quantitative process.

In the general context of the present invention, for an IR spectrum to correspond to another IR spectrum is for the IR spectrum in question to be similar to (e.g. to be substantially or essentially the same as) the reference IR spectrum. Thus, an IR spectrum in question corresponds to a reference IR spectrum if it is similar to, or substantially the same as, or equivalent to, or matches or fits, the reference IR spectrum e.g. it is statistically similar or statistically equivalent.

In the practice of this aspect of the invention the IR spectrum for the sample of body fluid may be considered to correspond to the IR spectrum for the alginate oligomer if it comprises one or more peaks at the wavenumbers at which the IR spectrum for the alginate oligomer has peaks. Preferably the spectrum may be considered to correspond if the IR spectrum for the sample of body fluid comprises peaks at all of the wavenumbers at which the IR spectrum for the alginate oligomer has peaks.

In one embodiment the IR spectrum for the sample of body fluid and the IR spectrum for the alginate oligomer are compared visually, or with analogous technologically assisted means. In other embodiments the steps of comparing the IR spectrum for the sample of body fluid and the IR spectrum for the alginate oligomer and determining whether or not they correspond may be performed using mathematical or statistical techniques, and generally this will be implemented by software (i.e. it will be performed using a computer). It may be determined whether the IR spectrum for the sample of body fluid is statistically more similar to the IR spectrum for the alginate oligomer than not.

Statistical or mathematical methods for performing such a comparison and determination of correspondence are well known and widely available in the art. In certain embodiments a non-parametric correlation analysis, e.g. Spearman's Rank, Kendall's Tau and/or point biserial correlation may be performed. In certain embodiments Spearman's Rank is performed.

It will be understood that the IR spectrum for the alginate oligomer will typically be prepared prior to performing the method of the invention and thus "providing" the IR spectrum for the alginate oligomer may refer in some embodiments to the provision of pre-prepared information, e.g. from an existing database, and in others to steps in which said IR spectrum is prepared as part of the method of the invention.

The method of the invention provides an indication of whether or not the body fluid sample contains an alginate oligomer. Thus the method may discriminate between body fluid samples comprising alginate oligomers and body fluid samples which do not comprise alginate oligomers. In other terms, the method may be considered a method for detecting alginate oligomers in a sample of body fluid. In still further terms the method of the invention may be considered a method for "determining the likelihood", "determining the probability" or "ascertaining the probability" or "assesses the probability" of a sample of body fluid comprising an alginate oligomer. As will be clear from the following, the outcomes of these evaluations may be numerical, graphical or illustrative, and in turn each may be qualitative, semi-quantitative or quantitative.

In another aspect the invention provides a method for determining the presence or absence of an alginate oligomer in a sample of body fluid, said method comprising (i) obtaining an first IR spectrum for the sample of body fluid, wherein the first IR spectrum for the sample of body fluid is a normalised IR absorbance spectrum from the wavenumber range of about 1200 cm$^{-1}$ to about 900 cm$^{-1}$ or a normalised IR transmittance spectrum from the wavenumber range of about 1200 cm$^{-1}$ to about 900 cm$^{-1}$, (ii) obtaining a second IR spectrum for the sample of body fluid, wherein the second IR spectrum for the sample of body fluid is the second derivative of an IR absorbance spectrum from the wavenumber range of about 1200 cm$^{-1}$ to about 900 cm$^{-1}$ or the second derivative of an IR transmittance spectrum from the wavenumber range of about 1200 cm$^{-1}$ to about 900 cm$^{-1}$, (iii) providing a first IR spectrum for the alginate oligomer, wherein the first IR spectrum for the alginate oligomer is a normalised IR absorbance spectrum from the wavenumber range of about 1200 cm$^{-1}$ to about 900 cm$^{-1}$ when the first spectrum for the sample of body fluid is an absorbance spectrum, or a normalised IR transmittance spectrum from the wavenumber range of about 1200 cm$^{-1}$ to about 900 cm$^{-1}$ when the first IR spectrum for the sample of body fluid is a transmittance spectrum, (iv) providing a second IR spectrum for the alginate oligomer, wherein the second IR spectrum for the alginate oligomer is the second derivative of an IR absorbance spectrum from the wavenumber range of about 1200 cm$^{-1}$ to about 900 cm$^{-1}$ when the second spectrum for the sample of body fluid is an absorbance spectrum, or the second derivative of an IR transmittance spectrum from the wavenumber range of about 1200 cm$^{-1}$ to about 900 cm$^{-1}$ when the second spectrum for the sample of body fluid is a transmittance spectrum, (v) performing a non-parametric correlation analysis on the first IR spectrum for the sample of body fluid and the first IR spectrum for the alginate oligomer thereby producing a first correlation coefficient, (vi) performing a non-parametric correlation analysis on the second IR spectrum for the sample of body fluid and the second IR spectrum for the alginate oligomer thereby producing a second correlation coefficient, (vii) providing corresponding first correlation coefficients and second correlation coefficients for a plurality of samples of said body fluid which contain an alginate oligomer and corresponding first correlation coefficients and second correlation coefficients for a plurality of samples of said body fluid which do not contain an alginate oligomer as Cartesian coordinates in a two or three dimensional Cartesian coordinate system, and (viii) determining the presence or absence of an alginate oligomer in the sample of body fluid by determining the relative position of a Cartesian coordinate comprising the first and second correlation coefficients obtained in steps (v) and (vi) in the Cartesian coordinate system of step (vii), wherein
(a) collocation of said Cartesian coordinate comprising the first and second correlation coefficients obtained in steps (v) and (vi) with the Cartesian coordinates of the samples of said body fluid which do not contain an alginate oligomer is indicative that the sample does not contain an alginate oligomer, and
(b) collocation of said Cartesian coordinate comprising the first and second correlation coefficients obtained in steps (v) and (vi) with the Cartesian coordinates of the samples of said body fluid which do contain an alginate oligomer is indicative that the sample does contain an alginate oligomer.

It will be appreciated immediately by the skilled person that steps (i) to (iv) and (vii), and steps (v), (vi) and (vii), respectively, may be performed in any order or simultaneously.

It will be understood that the provision of corresponding first and second correlation coefficients for a plurality of samples of said body fluid which contain an alginate oligomer is a reference to the provision of first and second correlation coefficients which have been prepared in essentially the same way, i.e. using the same non-parametric correlation analysis, as the correlation coefficients prepared in accordance with steps (i) to (vi), but instead of using a test sample of body fluid which may or may not contain an alginate oligomer, equivalent samples of the body fluid which are known to contain an alginate oligomer are used. In other words, positive and negative reference (also referred to as a positive or negative control) samples of body fluid are used to prepare the corresponding first and second correlation coefficients. It will be apparent to the skilled person that the samples of body fluid used as reference samples (equivalent samples) should be essentially the same as the test samples, i.e. of the same type, obtained using essentially the same technique and subsequently stored and handled in essentially the same way. It will also be apparent to the skilled person that the most accurate model will be prepared when the alginate oligomer used in the reference samples is essentially the same as the alginate oligomer to be detected.

The Cartesian coordinate system may be provided as a graphical representation, e.g. a 2D or 3D scatter plot (scatter graph), in tabulated form, as a data matrix, or a computer readable representation thereof carried in a computer. In certain embodiments the Cartesian coordinate system is a 2D system and the coordinates are formed of the first and second correlation coefficients.

Collocation may be considered to occur if the coordinate from the test sample is substantially, e.g. essentially, at or within the outermost boundaries formed by the cluster of the coordinates of the positive or negative reference points. This may be determined by any convenient cluster analysis technique or algorithm.

In specific embodiments collocation is determined by application of a linear regression model generated from the corresponding analysis of body fluid samples known to contain an alginate oligomer and body fluid samples known not to contain an alginate oligomer. Thus in certain embodiments the invention provides a method for determining the presence or absence of an alginate oligomer in a sample of body fluid, said method comprising:

(i) obtaining an first IR spectrum for the sample of body fluid, wherein the first IR spectrum for the sample of body fluid is a normalised IR absorbance spectrum from the wavenumber range of about 1200 cm$^{-1}$ to about 900 cm$^{-1}$ or a normalised IR transmittance spectrum from the wavenumber range of about 1200 cm$^{-1}$ to about 900 cm$^{-1}$, (ii) obtaining a second IR spectrum for the sample of body fluid, wherein the second IR spectrum for the sample of body fluid is the second derivative of an IR absorbance spectrum from the wavenumber range of about 1200 cm$^{-1}$ to about 900 cm$^{-1}$ or the second derivative of an IR transmittance spectrum from the wavenumber range of about 1200 cm$^{-1}$ to about 900 cm$^{-1}$, (iii) providing a first IR spectrum for the alginate oligomer, wherein the first IR spectrum for the alginate oligomer is a normalised IR absorbance spectrum from the wavenumber range of about 1200 cm$^{-1}$ to about 900 cm$^{-1}$ when the first spectrum for the sample of body fluid is an absorbance spectrum, or a normalised IR transmittance spectrum from the wavenumber range of about 1200 cm$^{-1}$ to about 900 cm$^{-1}$ when the first IR spectrum for the sample of body fluid is a transmittance spectrum, (iv) providing a second IR spectrum for the alginate oligomer, wherein the second IR spectrum for the alginate oligomer is the second derivative of an IR absorbance spectrum from the wavenumber range of about 1200 cm$^{-1}$ to about 900 cm$^{-1}$ when the second spectrum for the sample of body fluid is an IR absorbance spectrum, or the second derivative of an IR transmittance spectrum from the wavenumber range of about 1200 cm$^{-1}$ to about 900 cm$^{-1}$ when the second spectrum for the sample of body fluid is a transmittance spectrum, (v) performing a non-parametric correlation analysis on the first IR spectrum for the sample of body fluid and the first IR spectrum for the alginate oligomer thereby producing a first correlation coefficient, (vi) performing a non-parametric correlation analysis on the second IR spectrum for the sample of body fluid and the second IR spectrum for the alginate oligomer thereby producing a second correlation coefficient, (vii) inputting the first correlation coefficient of step (v) into the linear prediction model Formula I $$Y=nX+m \qquad \text{Formula I}$$

as X and determining a value for Y, (viii) wherein a value for Y which is equal to or less than the second correlation coefficient of step (vi) is an indication that the alginate oligomer is present in the sample of body fluid, and a value for Y which is greater than the second correlation coefficient of step (vi) is an indication that the alginate oligomer is absent from the sample of body fluid, and wherein the linear regression model and has been prepared by (a) obtaining one or more normalised IR absorbance spectra or one or more normalised IR transmittance spectra from the wavenumber range of about 1200 cm$^{-1}$ to about 900 cm$^{-1}$ for a plurality of samples of said body fluid which contain the alginate oligomer and a plurality of samples of said body fluid which do not contain the alginate oligomer, (b) providing a normalised IR absorbance spectrum from the wavenumber range of about 1200 cm$^{-1}$ to about 900 cm$^{-1}$ for the alginate oligomer when the spectra of step (a) are IR absorbance spectra, or a normalised IR transmittance spectrum from the wavenumber range of about 1200 cm$^{-1}$ to about 900 cm$^{-1}$ for the alginate oligomer when the spectra of step (a) are IR transmittance spectra, (c) performing a non-parametric correlation analysis on the IR spectra of step (a) and the IR spectrum for the alginate oligomer of step (b) thereby producing at least one correlation coefficient for each of the samples of step (a); and (d) obtaining the second derivatives of one or more IR absorbance spectra or the second derivatives of one or more IR transmittance spectra from the wavenumber range of about 1200 cm$^{-1}$ to about 900 cm$^{-1}$ for the plurality of samples of said body fluid which contain the alginate oligomer and the plurality of samples of said body fluid which do not contain the alginate oligomer of step (a), (e) providing the second derivative of a normalised IR absorbance spectrum from the wavenumber range of about 1200 cm$^{-1}$ to about 900 cm$^{-1}$ for the alginate oligomer when the spectra of step (d) are the second derivatives of IR absorbance spectra, or the second derivative of a normalised IR transmittance spectrum from the wavenumber range of about 1200 cm$^{-1}$ to about 900 cm$^{-1}$ for the alginate oligomer when the spectra of step (d) are the second derivatives of IR transmittance spectra, (f) performing a non-parametric correlation analysis on the second derivatives of the IR spectra of step (d) and the second derivative of the IR spectrum for the alginate oligomer of step (e) thereby producing at least one further correlation coefficient for each of the samples of step (a); and (g) for each of the plurality of samples of step (a) plotting the further correlation coefficient produced in step (f) and the correlation coefficient produced in step (c) as a Cartesian coordinates in a two dimensional Cartesian coordinate system, and (h) determining the optimum separation of the Cartesian coordinates of the plurality of samples of said body fluid which contain the samples of said body fluid which do not contain the alginate oligomer to yield a separation threshold defined by the linear regression model Y=nX+m, wherein n and m are numerical constants, and X is a correlation coefficient of step (c) for a sample of step (a).

It will be appreciated immediately by the skilled person that steps (i) to (iv), steps (v) and (vi), steps (a) and (b), steps (d) and (e), and steps (a)-(c) and (d)-(f), respectively, may be performed in any order or simultaneously.

The Cartesian coordinate system may be provided as a graphical representation, e.g. a scatter plot (scatter graph), in tabulated form, as a data matrix, or a computer readable representation thereof carried in a computer.

The optimum separation of the Cartesian data may be achieved by any convenient means. This may be by manual application of suitable algorithms for by computer assisted means.

In more specific embodiments the method comprises performing steps (a) to (h) before, after or simultaneously with steps (i) to (viii), but this not essential and typically the linear prediction model will have been determined separately to the methods of the invention.

It will be apparent to the skilled person that the samples of body fluid used in the preparation of the linear prediction model should be essentially the same as the test samples, i.e. of the same type, obtained using essentially the same technique and subsequently stored and handled in essentially the same way. It will also be apparent to the skilled person that the most accurate model will be prepared when the alginate oligomer used is essentially the same as the alginate oligomer to be detected.

Thus, the linear prediction model may be Y=−1.96X+1.72 when the sample is sputum, e.g. sputum from a CF patient, and the alginate oligomer is an alginate oligomer of 5-20 monomer residues (which may be expressed as an alginate oligomer having a DPn of 13 or a weight average molecular weight of 3200 Da) of which 90-95% are G residues In other embodiments the concentration of alginate oligomer in the body fluid sample may be determined, e.g. quantified, by calculating the Euclidean Distance of the coordinates of the body fluid sample from the separation threshold defined by the linear regression model.

As shown in the Examples, the methods of the invention may detect the presence or absence of alginate oligomers in body fluid samples with a sensitivity of up to 86% and a specificity of up to 90%, i.e. an overall accuracy of up to 88% accuracy. Thus, in certain embodiments the sensitivity of the methods of the invention for detecting the presence or absence of alginate oligomers in body fluid samples is at least 70%, e.g. at least 75%, 80%, 85% or 90%. In other embodiments the specificity of the methods of the invention for detecting the presence or absence of alginate oligomers in body fluid samples is at least 75%, e.g. at least 80%, 85%, 90%, or 95%. In other embodiments the overall accuracy of the methods of the invention for detecting the presence or absence of alginate oligomers in body fluid samples is at least 70%, e.g. at least 75% 80%, 85%, 90% or 95%.

The invention further provides a method for determining the concentration of alginate oligomer in a sample of body fluid, said method comprising (a)(i) obtaining a first IR spectrum for the sample of body fluid, wherein the first IR spectrum for the sample of body fluid is a normalised IR absorbance spectrum from the wavenumber range of about 1200 cm$^{-1}$ to about 900 cm$^{-1}$ or a normalised IR transmittance spectrum from the wavenumber range of about 1200 cm$^{-1}$ to about 900 cm$^{-1}$, (a)(ii) providing a first IR spectrum for the alginate oligomer, wherein the first IR spectrum for the alginate oligomer is a normalised IR absorbance spectrum from the wavenumber range of about 1200 cm$^{-1}$ to about 900 cm$^{-1}$ when the first spectrum for the sample of body fluid is an absorbance spectrum, or a normalised IR transmittance spectrum from the wavenumber range of about 1200 cm$^{-1}$ to about 900 cm$^{-1}$ when the first IR spectrum for the sample of body fluid is a transmittance spectrum,
- (a)(iii) performing a non-parametric correlation analysis on the first IR spectrum for the sample of body fluid and the first IR spectrum for the alginate oligomer thereby producing a first correlation coefficient,
- (a)(iv) providing corresponding correlation coefficients for a plurality of samples of said body fluid which contain a range of known amounts of the alginate oligomer, and
- (a)(v) determining the concentration of the alginate oligomer in the sample of body fluid by determining the relative position of the first correlation coefficient obtained in step (a)(iii) amongst the correlation coefficients of step (a)(iv); or
- (b)(i) obtaining a second IR spectrum for the sample of body fluid, wherein the second IR spectrum for the sample of body fluid is the second derivative of an IR absorbance spectrum from the wavenumber range of about 1200 cm$^{-1}$ to about 900 cm$^{-1}$ or the second derivative of an IR transmittance spectrum from the wavenumber range of about 1200 cm$^{-1}$ to about 900 cm$^{-1}$,
- (b)(ii) providing a second IR spectrum for the alginate oligomer, wherein the second IR spectrum for the alginate oligomer is the second derivative of an IR absorbance spectrum from the wavenumber range of about 1200 cm$^{-1}$ to about 900 cm$^{-1}$ when the second spectrum for the sample of body fluid is an absorbance spectrum, or the second derivative of an IR transmittance spectrum from the wavenumber range of about 1200 cm$^{-1}$ to about 900 cm$^{-1}$ when the second spectrum for the sample of body fluid is a transmittance spectrum,
- (b)(iii) performing a non-parametric correlation analysis on the second IR spectrum for the sample of body fluid and the second IR spectrum for the alginate oligomer thereby producing a second correlation coefficient,
- (b)(iv) providing corresponding correlation coefficients for a plurality of samples of said body fluid which contain a range of known amounts of the alginate oligomer, and
- (b)(v) determining the concentration of the alginate oligomer in the sample of body fluid by determining the relative position of the second correlation coefficient obtained in step (b)(iii) amongst the correlation coefficients of step (b)(iv).

It will be appreciated immediately by the skilled person that steps (a)(i) and (a)(ii), steps (a)(iii) and (a)(iv), steps (b)(i) and (b)(ii), steps (b)(iii) and (b)(iv), respectively, may be performed in any order or simultaneously.

In accordance with the invention, a method of "determining the concentration of an alginate oligomer" may alternatively be considered a method of "determining the amount of an alginate oligomer" or "determining the level of an alginate oligomer" in a sample of known volume. Such methods may be considered methods for quantifying or measuring the concentration/amount of alginate oligomer in the sample. In other embodiments the determination may be semi-quantitative and in these embodiments the method may be considered method for estimating the concentration/amount of alginate oligomer in the sample.

It will be understood that references herein to a plurality of samples of said body fluid which contain a range of known amounts of the alginate oligomer is a reference to a plurality of samples of said body fluid at least some of which each contain different known amounts of the alginate oligomer and as such together provide a range of known amounts of the alginate oligomer.

It will also be understood that the provision of corresponding correlation coefficients for a plurality of samples of said body fluid which contain a range of known amounts of the alginate oligomer is a reference to the provision of correlation coefficients which have been prepared in essentially the same way, i.e. using the same non-parametric correlation analysis, as the correlation coefficients prepared in accordance with steps (a)(i) to (a)(iii) or (b)(i) to (b)(iii), but instead of using a test sample of body fluid containing an unknown concentration of alginate oligomers, equivalent samples of the body fluid at least some of which each contain different known concentrations of alginate oligomers are used. In other words, reference (or positive control) samples of body fluid are used to prepare the corresponding correlation coefficients. It will be apparent to the skilled person that the samples of body fluid used as reference samples (equivalent samples) should be essentially the same as the test samples, i.e. of the same type, obtained using essentially the same technique and subsequently stored and handled in essentially the same way. It will also be apparent to the skilled person that the most accurate model will be prepared when the alginate oligomer used in the reference samples is essentially the same as the alginate oligomer to be detected.

In certain embodiments the corresponding correlation coefficients are conveniently arranged in a tabulated form, or as a data matrix, i.e. a two dimensional array of data elements, or as Cartesian coordinates in a two dimensional Cartesian coordinate system, in which the various alginate oligomer concentrations of each of said plurality of samples of said body fluid which contain a range of known amounts of the alginate oligomer is arranged in one dimension. The use of a Cartesian coordinate system which is a graphical representation, e.g. a scatter plot (scatter graph), may be most convenient for human analysis, but this is not essential, and in other embodiments computer readable representations of the abovementioned arrangements may be provided for analysis by a computer. A graphical representation of the Cartesian coordinate system of use herein may be referred to simply as a standard curve, or a calibration curve, and the position of the Cartesian coordinates of the sample under test on such a curve is an indication of the concentration of alginate oligomer in the test sample.

The invention further provides a method for determining the concentration of alginate oligomer in a sample of body fluid, said method comprising
- (i) obtaining an first IR spectrum for the sample of body fluid, wherein the first IR spectrum for the sample of body fluid is a normalised IR absorbance spectrum from the wavenumber range of about 1200 cm$^{-1}$ to about 900 cm$^{-1}$ or a normalised IR transmittance spectrum from the wavenumber range of about 1200 cm$^{-1}$ to about 900 cm$^{-1}$,
- (ii) obtaining a second IR spectrum for the sample of body fluid, wherein the second IR spectrum for the sample of body fluid is the second derivative of an IR absorbance spectrum from the wavenumber range of about 1200 cm$^{-1}$ to about 900 cm$^{-1}$ or the second derivative of an IR transmittance spectrum from the wavenumber range of about 1200 cm$^{-1}$ to about 900 cm$^{-1}$,
- (iii) providing a first IR spectrum for the alginate oligomer, wherein the first IR spectrum for the alginate oligomer is a normalised IR absorbance spectrum from the wavenumber range of about 1200 cm$^{-1}$ to about 900 cm$^{-1}$ when the first IR spectrum for the sample of body fluid is an absorbance spectrum, or a normalised IR transmittance spectrum from the wavenumber range of about 1200 cm$^{-1}$ to about 900 cm$^{-1}$ when the first IR spectrum for the sample of body fluid is a transmittance spectrum, (iv) providing a second IR spectrum for the alginate oligomer, wherein the second IR spectrum for the alginate oligomer is the second derivative of an IR absorbance spectrum from the wavenumber range of about 1200 cm$^{-1}$ to about 900 cm$^{-1}$ when the second IR spectrum for the sample of body fluid is an IR absorbance spectrum, or the second derivative of an IR transmittance spectrum from the wavenumber range of about 1200 cm$^{-1}$ to about 900 cm$^{-1}$ when the second IR spectrum for the sample of body fluid is an IR transmittance spectrum, (v) performing a non-parametric correlation analysis on the first IR spectrum for the sample of body fluid and the first IR spectrum for the alginate oligomer thereby producing a first correlation coefficient, (vi) performing a non-parametric correlation analysis on the second IR spectrum for the sample of body fluid and the second IR spectrum for the alginate oligomer thereby producing a second correlation coefficient, (vii) providing corresponding first correlation coefficients and second correlation coefficients for a plurality of samples of said body fluid which contain a range of known concentrations of the alginate oligomer as Cartesian coordinates in a two or three dimensional Cartesian coordinate system, and (viii) determining the concentration of the alginate oligomer in the sample of body fluid by determining the relative position of a Cartesian coordinate comprising the first and second correlation coefficients obtained in steps (v) and (vi) in the Cartesian coordinate system of step (vii).

It will be appreciated immediately by the skilled person that steps (i) to (iv) and (vii), steps (v), (vi) and (vii), and step (v) and step (vi), respectively, may be performed in any order or simultaneously.

As mentioned already, it will be understood that references herein to a plurality of samples of said body fluid which contain a range of known amounts of the alginate oligomer is a reference to a plurality of samples of said body fluid at least some of which each contain different known amounts of the alginate oligomer and as such together provide a range of known amounts of the alginate oligomer.

It will also be understood that the provision of corresponding first and second correlation coefficients for a plurality of samples of said body fluid which contain a range of known amounts of the alginate oligomer is a reference to the provision of first and second correlation coefficients which have been prepared in essentially the same way, i.e. using the same non-parametric correlation analysis, as the correlation coefficients prepared in accordance with steps (i) to (vi), but instead of using a test sample of body fluid containing an unknown concentration of alginate oligomers, equivalent samples of the body fluid at least some of which each contain different known concentrations of alginate oligomers are used. In other words, reference (or positive control) samples of body fluid are used to prepare the corresponding first and second correlation coefficients. It will be apparent to the skilled person that the samples of body fluid used as reference samples (equivalent samples) should be essentially the same as the test samples, i.e. of the same type, obtained using essentially the same technique and subsequently stored and handled in essentially the same way. It will also be apparent to the skilled person that the most accurate model will be prepared when the alginate oligomer used in the reference samples is essentially the same as the alginate oligomer to be detected.

In certain embodiments the Cartesian coordinate system is a 2D system and the coordinates are formed of the first and second correlation coefficients.

In certain embodiments the Cartesian coordinated of the corresponding first and second correlation coefficients are conveniently arranged in a graphical representation, e.g. a 2D or 3D scatter plot (scatter graph), but this is not essential, and in other embodiments computer readable representation may be provided for analysis by a computer. A graphical representation of the Cartesian coordinate system of use herein may be referred to simply as a standard curve, or a calibration curve, and the position of the Cartesian coordinates of the sample under test on such a curve is an indication of the concentration of alginate oligomer in the test sample.

The invention further provides a method for determining the concentration of alginate oligomer in a sample of body fluid, said method comprising (i) obtaining for the sample of body fluid one or more normalised IR absorbance values, one or more normalised IR transmittance values, one or more second derivative IR absorbance values, or one or more second derivative IR transmittance values, at one or more wavenumbers selected from one or more of the following wavenumber ranges:
  (a) 1596 cm$^{-1}$ to 1606 cm$^{-1}$,
  (b) 1407 cm$^{-1}$ to 1417 cm$^{-1}$,
  (c) 1120 cm$^{-1}$ to 1130 cm$^{-1}$,
  (d) 1081 cm$^{-1}$ to 1091 cm$^{-1}$,
  (e) 1023 cm$^{-1}$ to 1033 cm$^{-1}$, and
  (f) 943 cm$^{-1}$ to 953 cm$^{-1}$;

(ii) for one or more of the wavenumbers selected in step (i) providing corresponding IR absorbance values, IR transmittance values, second derivative IR absorbance values, or second derivative IR transmittance values, for a plurality of samples of said body fluid which contain a range of known amounts of the alginate oligomer, and (iii) determining the concentration of the alginate oligomer in the sample of body fluid by determining the relative position of the values obtained in step (i) amongst the values provided in step (ii)

As mentioned already, it will be understood that references herein to a plurality of samples of said body fluid which contain a range of known amounts of the alginate oligomer is a reference to a plurality of samples of said body fluid at least some of which each contain different known amounts of the alginate oligomer and as such together provide a range of known amounts of the alginate oligomer.

It will also be understood that the provision of corresponding IR absorbance values, IR transmittance values, second derivative IR absorbance values, or second derivative IR transmittance values for a plurality of samples of said body fluid which contain a range of known amounts of the alginate oligomer is a reference to the provision of IR absorbance values, IR transmittance values, second derivative IR absorbance values, or second derivative IR transmittance values which have been prepared in essentially the same way as the IR absorbance values, IR transmittance values, second derivative IR absorbance values, or second derivative IR transmittance values in accordance with step (i), but instead of using a test sample of body fluid containing an unknown concentration of alginate oligomers, equivalent samples of the body fluid at least some of which each contain different known concentrations of alginate oligomers are used. In other words, reference (also referred to as positive control) samples of body fluid are used to prepare the corresponding IR absorbance values, IR transmittance values, second derivative IR absorbance values, or second derivative IR transmittance values. It will be apparent to the skilled person that the samples of body fluid used as reference samples (also referred to as equivalent samples) should be essentially the same as the test samples, i.e. of the same type, obtained using essentially the same technique and subsequently stored and handled in essentially the same way. It will also be apparent to the skilled person that the most accurate model will be prepared when the alginate oligomer used in the reference samples is essentially the same as the alginate oligomer to be detected.

It will also be understood that the corresponding IR absorbance values, IR transmittance values, second derivative IR absorbance values, or second derivative IR transmittance values for a plurality of samples of said body fluid which contain a range of known amounts of the alginate oligomer will typically be prepared prior to performing the method of the invention and thus "providing" the corresponding IR absorbance values, IR transmittance values, second derivative IR absorbance values, or second derivative IR transmittance values for a plurality of samples of said body fluid which contain a range of known amounts of the alginate oligomer may refer in some embodiments to the provision of pre-prepared information, e.g. from an existing database, and in others to steps in which said corresponding IR absorbance values, IR transmittance values, second derivative IR absorbance values, or second derivative IR transmittance values for a plurality of samples of said body fluid which contain a range of known amounts of the alginate oligomer are prepared as part of the method of the invention.

In certain embodiments the corresponding IR absorbance values, IR transmittance values, second derivative IR absorbance values, or second derivative IR transmittance values for a plurality of samples of said body fluid which contain a range of known amounts of the alginate oligomer are conveniently arranged in a tabulated form, or as a data matrix, i.e. a two dimensional array of data elements, or as Cartesian coordinates in a two dimensional Cartesian coordinate system, in which the various alginate oligomer concentrations of each of said plurality of samples of said body fluid which contain a range of known amounts of the alginate oligomer are arranged in one dimension. The use of a Cartesian coordinate system which is a graphical representation, e.g. a scatter plot (scatter graph), may be most convenient for human analysis, but this is not essential, and in other embodiments computer readable representations of the abovementioned arrangements may be provided for analysis by a computer. A graphical representation of the Cartesian coordinate system of use herein may be referred to simply as a standard curve, or a calibration curve, and the position of the Cartesian coordinates of the sample under test on such a curve is an indication of the concentration of alginate oligomer in the test sample.

In certain embodiments the wavenumber range of (a) may be 1597 $cm^{-1}$ to 1605 $cm^{-1}$, 1598 $cm^{-1}$ to 1604 $cm^{-1}$, 1599 $cm^{-1}$ to 1603 $cm^{-1}$, 1600 $cm^{-1}$ to 1602 $cm^{-1}$, or about 1601 $cm^{-1}$. Any other ranges derived from these various range endpoints are specifically contemplated.

In certain embodiments, the wavenumber range of (b) may be 1408 $cm^{-1}$ to 1416 $cm^{-1}$, 1409 $cm^{-1}$ to 1415 $cm^{-1}$, 1410 $cm^{-1}$ to 1414 $cm^{-1}$, 1411 $cm^{-1}$ to 1413 $cm^{-1}$, or about 1412 $cm^{-1}$. Any other ranges derived from these various range endpoints are specifically contemplated.

In certain embodiments, the wavenumber range of (c) may be 1121 $cm^{-1}$ to 1129 $cm^{-1}$, 1122 $cm^{-1}$ to 1128 $cm^{-1}$, 1123 $cm^{-1}$ to 1127 $cm^{-1}$, 1124 $cm^{-1}$ to 1126 $cm^{-1}$, or about 1125 $cm^{-1}$. Any other ranges derived from these various range endpoints are specifically contemplated.

In certain embodiments, the wavenumber range of (d) may be 1082 $cm^{-1}$ to 1090 $cm^{-1}$, 1083 $cm^{-1}$ to 1089 $cm^{-1}$, 1084 $cm^{-1}$ to 1088 $cm^{-1}$, 1085 $cm^{-1}$ to 1087 $cm^{-1}$, or about 1086 $cm^{-1}$. Any other ranges derived from these various range endpoints are specifically contemplated.

In certain embodiments, the wavenumber range of (e) may be 1024 $cm^{-1}$ to 1032 $cm^{-1}$, 1025 $cm^{-1}$ to 1031 $cm^{-1}$, 1026 $cm^{-1}$ to 1030 $cm^{-1}$, 1027 $cm^{-1}$ to 1029 $cm^{-1}$, or about 1028 $cm^{-1}$. Any other ranges derived from these various range endpoints are specifically contemplated.

In certain embodiments, the wavenumber range of (f) may be 944 $cm^{-1}$ to 952 $cm^{-1}$, 945 $cm^{-1}$ to 951 $cm^{-1}$, 946 $cm^{-1}$ to 950 $cm^{-1}$, 947 $cm^{-1}$ to 949 $cm^{-1}$, or about 948 $cm^{-1}$. Any other ranges derived from these various range endpoints are specifically contemplated.

In certain embodiments step (i) of this aspect comprises obtaining for the sample of body fluid one or more normalised IR absorbance values, one or more normalised IR transmittance values, one or more second derivative IR absorbance values, or one or more second derivative IR transmittance values at one or more wavenumbers selected from two or more, three or more, four or more, five or more, or all of the above recited wavenumber ranges. In other embodiments one, two, three or four of wavenumber ranges (c) to (f), e.g. (d) and/or (e), in particular (e) are used.

In certain embodiments of this aspect of the invention one or more of the IR absorbance, IR transmittance values, second derivative IR absorbance values or second derivative IR transmittance values, at the wavenumber ranges recited above are provided as part of a continuous IR spectrum, or portions thereof, covering one or more of the wavenumber ranges recited above. Thus, the method may be performed by preparing, or generating, an IR spectrum, for each sample, or each sample replicate, across a wavenumber range which includes one or more of the six ranges specified above, for example the range 4000-450 $cm^{-1}$, or a smaller part of this range e.g. 1800-700 $cm^{-1}$ or 1200-900 $cm^{-1}$, or 1100-1000 $cm^{-1}$, etc.

The IR absorbance or IR transmittance spectra and the IR absorbance or IR transmittance values at the wavenumber ranges on which the method of the invention are based may be prepared by any IR (infrared) spectrometer (alternatively referred to as a spectrophotometer, which terms are used interchangeably herein) capable of producing IR light at the required wavenumber range or ranges and measuring IR absorbance and/or IR transmittance. The spectrometer is preferably a portable device, more preferably a hand-held device. Preferably, a single device will be used, but this is not essential. In preferred embodiments, a Fourier transform infrared (FTIR) spectrometer is used, however devices which measure absorbance or transmittance at monochromatic wavelengths may also be used. In further embodiments the preparation of IR absorbance or IR transmittance values/spectra may, at least in part, comprise the use of a transmission or an attenuated total reflection (ATR) technique to apply the IR radiation to the sample. However, the invention is by no means limited to the use of ATR-FTIR spectrometers or transmission-FTIR spectrometers and, for instance, a diffuse reflectance infrared Fourier transform (DRIFT) spectrometer may be used to execute a diffuse reflectance FTIR technique. Thus, in one preferred embodiment the IR absorbance and/or transmittance values/spectra are FTIR values/spectra, and more particularly ATR-FTIR values/spectra or transmission FTIR values/spectra. Portable and hand-held IR spectrometers, including FTIR spectrometers, are well known in the art and commercially available from a variety of manufacturers. It may be advantageous to use devices which are configured to use disposable sample containers or strips to which the sample of body fluid may be applied or collected within.

In the methods of the invention the steps of obtaining an IR spectrum or IR absorbance or IR transmittance values for the sample of body fluid may, independently, further comprise a step in which the one or more of the normalised IR absorbance or normalised IR transmittance values/spectra is prepared from the test sample of body fluid, e.g. a step in which the test sample of body fluid is analysed with an IR spectrometer, preferably an FTIR spectrometer, e.g. an ATR-FTIR or a transmission FTIR or a DRIFT spectrometer, and one or more IR absorbance or IR transmittance values/spectra at one or more of said wavenumber ranges is obtained. These values are then normalised, e.g. as described below.

In other embodiments the of the invention the steps of obtaining an IR spectrum for the sample of body fluid may, independently, comprise a step in which the second derivative of an IR spectra may be prepared as described above. In still further embodiments the step of providing an IR spectra from which the second derivative is prepared further comprises a step in which one or more IR absorbance or IR transmittance spectra is prepared from the test sample of body fluid, e.g. a step in which the test sample of body fluid is analysed with an IR spectrometer, preferably an FTIR spectrometer, e.g. an ATR-FTIR or a transmission FTIR or a DRIFT spectrometer, and one or more IR absorbance or IR transmittance spectra at one or more of said wavenumber ranges is obtained.

Analogously, in the methods of the invention the steps of providing an IR spectrum for the alginate oligomer may, independently, comprise a step in which the one or more of the normalised IR absorbance or normalised IR transmittance spectra is prepared from the a sample of the alginate oligomer, e.g. a step in which a sample of the alginate oligomer is analysed with an IR spectrometer, preferably an FTIR spectrometer, e.g. an ATR-FTIR or a transmission FTIR or a DRIFT spectrometer, and one or more IR absorbance or IR transmittance spectra at one or more of said wavenumber ranges is obtained. These spectra are then normalised, e.g. as described below. The second derivative of IR absorbance or IR transmittance spectra for an alginate oligomer may then be prepared analogously as described above. In accordance with the invention, an IR spectrum for the alginate oligomer may be prepared from a 0.2% w/v solution of the alginate oligomer in distilled water.

The preparation of said IR absorbance or IR transmittance values/spectra will typically involve the subtraction of an internal background reading to allow for the contribution the apparatus and other components of the system make to the values/spectra obtained. For example, background readings in the absence of sample can be taken (e.g. a background spectrum can be generated) and may be subtracted from the readings (e.g. spectrum) taken in the presence of sample (i.e. the test or "sample" readings or spectrum). In certain embodiments references to IR absorbance and IR transmittance spectra/values is a reference to spectra/values which have undergone such background correction.

It may further be convenient to prepare said IR absorbance or IR transmittance values/spectra for a sample from a plurality of individual readings from a single aliquot from the sample, in other words multiple readings at a given or selected wavenumber, or within a given wavenumber range, from a single aliquot from the sample may be obtained. For example, at least 2, preferably at least 3, e.g. at least 4, 5, 6, 8 or 10 readings may be obtained. These values may be used to derive a mean value for a given wavenumber or wavenumber range, or an average spectrum for a wavenumber range.

In other embodiments at least one reading at a given or selected wavenumber, or within a given wavenumber range, or from across a given wavenumber range from multiple replicates of the sample are taken. For example, at least one reading (e.g. as described above) from at least 2, preferably at least 3, e.g. at least 4, 5, 6, 8 or 10 replicates may be obtained. These values may be used to derive a mean value for a given wavenumber, or for a given wavenumber range, or an average spectrum for a wavenumber range.

Said individual readings/replicates may be selected (or omitted) on the basis of a similarity (or dissimilarity) measure where only those individual readings/replicates of sufficient similarity (or lack of dissimilarity) are selected. A suitable measure of dissimilarity is the spectral distance (D), i.e. (1−Pearson's correlation coefficient)×1000, and in preferred embodiments only those replicates having a D value of equal to or less than 10, e.g. equal to or less than 8, 6, 5, 4, 3, 2 or 1 are selected.

Normalisation of the IR absorbance or IR transmittance values/spectra for the samples of body fluid and the samples of alginate oligomer may be achieved with any convenient statistical means, e.g. Min-Max or vector normalisation. It may be convenient to measure absorbance values (or transmittance values, if appropriate) at a further wavenumber (the "normalisation wavenumber") and then apply a weighting to the remaining values/part of the spectrum which is the weighting which must be applied to the value at the further wavenumber to ensure all spectra being compared have equal values at the further wavenumber. The further (normalisation) wavenumber may conveniently be outside the wavenumber ranges recited herein. In certain embodiments said further ("normalisation") wavenumber is that which represents the peak of greatest IR absorbance or the least IR transmission, e.g. the Amide I wavenumber, i.e. about 1640 $cm^{-1}$, e.g. 1635 $cm^{-1}$ to 1645 $cm^{-1}$, preferably 1637 $cm^{-1}$ to 1643 $cm^{-1}$ or 1639 $cm^{-1}$ to 1641 $cm^{-1}$.

In certain embodiments the IR absorbance or IR transmittance values/spectra are normalised on a scale of 0-2.0 with maximum absorbance (minimum transmission) being set at 2.0 and minimum absorbance (maximum transmission) being set at 0. The skilled person will however be capable of converting such a scale into a scale of alternative dimensions, e.g. a percentage scale may be used, or into an additive inverse (negative) scale.

In other embodiments the IR absorbance and IR transmittance spectra/values (e.g. background corrected spectra/values) may undergo baseline correction to provide a baseline which is not substantially curved, e.g. is essentially level or flat, thereby permitting more accurate analysis, e.g. comparison/correlation analysis, of the IR absorbance and IR transmittance spectra/values. If the IR absorbance and IR transmittance spectra/values are to be normalised, baseline correction will typically be applied before normalisation, but this is not essential.

In certain embodiments the methods of the invention the IR spectra/values are IR absorbance spectra/values.

It will be understood by the skilled person that the IR absorbance and the IR transmittance for a sample are related by the equation of Formula II $$\text{Abs}=2-\log_{10}(T) \quad \text{Formula II}$$

and the steps of the method of the invention in which IR absorbance or IR transmittance values/spectra are obtained or provided encompass intermediate steps in which IR absorbance or IR transmittance values/spectra are prepared and converted to IR transmittance or IR absorbance values/spectra, respectively, as required.

The method of this aspect of the invention is an in vitro method insofar as it is performed on a sample of body fluid which has been obtained, or isolated, from a subject. In other words the method is not performed in vivo, or is not performed on the body of a subject. In more specific aspects the method may further include a step in which the sample is obtained or isolated from a subject, preferably non-surgically or non-invasively. Thus, unless explicated indicated otherwise, the treatment of a subject with an alginate oligomer (i.e. the step of administering an alginate oligomer before or after performing the method of the invention) is not part of the method of the invention.

The methods of the invention may therefore be performed on a computer, system or apparatus carrying a program adapted to perform said methods. Thus, the methods of the invention may be computer-implemented methods and the invention further provides a computer, system or apparatus configured to, e.g. carrying a program adapted to, perform the methods of the invention or certain steps thereof. The system or apparatus may be further adapted to prepare IR absorbance or IR transmittance spectra/values at one or more of the wavenumber ranges of the invention, or a step thereof, e.g. the step that results in an IR spectrum of use in accordance with the present invention, preferably in a partially or fully automated manner. The system or apparatus may be further adapted to prepare second derivative IR absorbance or IR transmittance spectra/values. The invention thus provides an IR spectrometer (e.g. an FTIR spectrometer), preferably portable or hand-held, configured or adapted to, e.g. carrying a program adapted to, perform the methods of the invention or certain steps thereof. The invention further provides a computer readable medium carrying said program and such a program per se. In still further aspects the invention provides Formula I and the use thereof in the types of methods described generally herein and the specific methods of the invention recited herein.

The results (final output) from the methods of the invention may be provided on computer or human readable media or communicated by any suitable means, electronic or otherwise, for comprehension and/or further interpretation by a skilled person.

A body fluid (also termed bodily fluid) is considered to be any fluid produced by the human or animal body. A sample of body fluid is a portion of body fluid which has been isolated from a human or animal body. The sample may comprise the body fluid in form in which it has been isolated or in a processed form (e.g. a form in which solids (e.g. cells, cell debris, fats, food particles) or water have been removed e.g. by centrifugation, filtration, chromatographic separation, evaporation or lyophilisation). In other embodiments the body fluid may be diluted with an aqueous solvent, e.g. water or a physiological buffer. In certain embodiments the body fluid is analysed in an essentially unmodified, i.e. natural, state. In other words, the sample of body fluid may be analysed in the form in which the body fluid has been collected from a subject.

Examples of body fluid include, but are not necessarily limited to, amniotic fluid, bile, blood, breast milk, cerebrospinal fluid, cerumen (earwax), chyle, chime, endolymph, faeces, female ejaculate, gastric juice, humour (e.g. aqueous and vitreous), lymph, mucus (e.g. sputum and nasal discharge), pericardial fluid, perilymph, peritoneal fluid, plasma, pleural fluid, pus, saliva, sebum (skin oil), serum, semen, sputum, sweat, tears, vaginal secretion, vomit, urine, and wound exudate. In certain embodiments the body fluid of use in accordance with the invention is an aqueous fluid, i.e. is predominantly a water based composition. In other embodiments the body fluid of use in accordance with the invention is selected from blood, cerebrospinal fluid, faeces, gastric juice, lymph, mucus, plasma, pus, saliva, serum, semen, sweat, tears, vaginal secretion, vomit, urine and wound exudate. Mucus (e.g. sputum) is of particular importance.

The term "mucus" is used herein in its broadest sense to refer to the material which coats mucosal surfaces of a mammal. Depending on the location of the mucosal surface in question and/or any pathological processes present at that location or in the host organism as a whole, the constituents of mucus found at that location may vary. At its most basic mucus can be considered to a simple gel-like mixture of mucin glycoproteins and electrolytes secreted by epithelial surfaces. In a physiological setting the mixture is inevitably more complex and other biomaterials, including cells (microbes and those from the host, e.g. inflammatory cells), cell debris, viruses and biomolecules (e.g. proteins, nucleic acids, lipids and polysaccharides) secreted from such cells will be present. In mucus of the respiratory system abiotic particulates (e.g. dust and smoke) may also be present in the mixture. In healthy subjects this heterogeneous mixture of mucin matrix and other biomaterials is efficiently cleared by the normal processes of mucus clearance in the body. In subjects with cystic fibrosis transmembrane conductance regulator (CFTR) dysfunction (e.g. subjects with cystic fibrosis), however, the basic mucin matrix is itself dysfunctional and therefore inherently resistant to efficient clearance. Reduced clearance means greater amounts of non-mucin components can accumulate in the mucus of subjects with CFTR dysfunction as compared to equivalent mucus in healthy subjects and this in turn further exacerbates the difficulties of mucus clearance and can lead to pathological effects from increased microbial colonisation. Thus, the term "mucus" may refer to a material of varying composition depending on the context in which the term is used, but this is entirely consistent with the manner with which the term is used in the art and the skilled person would recognise and understand the use of the term in the context of the present invention to mean essentially the mucous material which may be present on any mucosal surface. In contrast, the term "sputum" is used herein to refer specifically to mucus from the respiratory system which has been expectorated.

The mucus on which the methods of the invention may be performed may therefore mucus from the respiratory system, e.g. those regions recited herein, the GI tract, the reproductive tract, the urinary tract, the pancreatic duct, and the bile duct. Suitable mucus collection techniques will depend on the target area, but in general can include sputum collection (respiratory tract), swabbing (e.g. nose, mouth and throat, lower GI tract and lower female reproductive tract), mucus biopsy and tissue biopsy, e.g. via an endoscopic procedure. Such procedures include esophagogastroduodenoscopy (oesophagus, stomach and duodenum), enteroscopy (small intestine), colonoscopy, (colon), sigmoidoscopy (large intestine) cholangioscopy (bile and pancreatic ducts), rectoscopy (rectum), anoscopy (anus), proctoscopy (anus and rectum), rhinoscopy (nose/sinus), bronchoscopy (lower respiratory tract), otoscopy (ear), cystoscopy (urinary tract), gynoscopy (female reproductive system), colposcopy (cervix), hysteroscopy (uterus), fallopoguscopy (fallopian tubes), laparoscopy (abdominal or pelvic cavity). Conveniently, however, the sample is sputum. Sputum collection is a widely practiced technique which simply involves a subject expectorating (or "coughing up") mucus from the lower respiratory tract.

The subject may be any human or non-human animal subject, but more particularly may be a human or non-human vertebrate, e.g. a non-human animal selected from mammals, birds, amphibians, fish and reptiles. The non-human animal may be a livestock or a domestic animal or an animal of commercial value, including laboratory animals or an animal in a zoo or game park. Representative non-human animals therefore include dogs, cats, horses, pigs, sheep, goats, cows, chickens, turkeys, guinea fowl, ducks and geese. Veterinary uses of the invention are thus covered. The subject may be viewed as a patient.

The subject may be of any age, e.g. may be a new-born, an infant, a child, a juvenile, an adolescent or an adult. For a human subject, the subject may be at least 5 years old, e.g. at least 6, 7, 8, 9, 10, 11, 12, 13, 14, 15, 16, 17 or 18 years old.

In certain embodiments the subject is a subject with an infection (e.g. bacterial, viral, fungal or parasitic infections), bacteraemia, sepsis, septic shock; a burn, an acute and/or chronic wound, reduced or abrogated epithelial or endothelial secretion (e.g. mucous, tears, saliva) and/or secretion clearance (e.g. subjects with poorly functioning cilia on mucosal tissue and/or subjects with hyperviscous mucous (e.g. smokers and subjects with COPD, COAD, COAP, bronchitis, cystic fibrosis, CFTR gene mutation heterozygosity, emphysema, bronchiectasis, lung cancer, asthma, pneumonia or sinusitis)), subjects fitted with a medical device, subjects in need of anticoagulation therapy (e.g. subjects with venous thrombosis, arterial thrombosis, atherosclerosis, vein graft failure, arterial graft failure, stroke, cardiac infarction, pulmonary embolism or thrombophilia).

In certain embodiments the subject is a human patient with CFTR ion channel dysfunction, more specifically a pathological phenotype, e.g. abnormal mucus and mucus clearance, associated with CFTR dysfunction. In particular embodiments the subject will be a human patient with CF. The terms "subject with CF", subject suffering from CF", "subject having CF" and "CF subject" are considered to be equivalent and are used interchangeably herein.

As noted above, alginates typically occur as polymers of an average molecular mass of at least 35,000 Daltons, i.e. approximately 175 to approximately 190 monomer residues, and an alginate oligomer may be defined as a material obtained by fractionation (i.e. size reduction) of an alginate polymer, commonly a naturally occurring alginate. An alginate oligomer can therefore be considered to be an alginate of an average molecular weight of less than 35,000 Daltons (i.e. less than approximately 190 or less than approximately 175 monomer residues), in particular an alginate of an average molecular weight of less than 30,000 Daltons (i.e. less than approximately 175 or less than approximately 150 monomer residues) more particularly an average molecular weight of less than 25,000 or 20,000 Daltons (i.e. less than approximately 135 or 125 monomer residues or less than approximately 110 or 100 monomer residues).

Viewed alternatively, an oligomer generally comprises 2 or more monomer units or residues up to the above mentioned size limits and an alginate oligomer according to the invention will typically contain 2 to 100 monomer residues, more typically 3, 4, 5 or 6 to 100, and may contain 2, 3, 4, 5 or 6 to 75, 2, 3, 4, 5 or 6 to 50, 2, 3, 4, 5 or 6 to 40, 2, 3, 4, 5 or 6 to 35 or 2, 3, 4, 5 or 6 to 30 residues. Thus, an alginate oligomer according to the invention will typically have an average molecular weight of 350, 550, 700, 900 or 1000 to 20,000 Daltons, 350, 550, 700, 900 or 1000 to 15,000 Daltons, 350, 550, 700, 900 or 1000 to 10,000 Daltons, 350, 550, 700, 900 or 1000 to 8000 Daltons, 350, 550, 700, 900 or 1000 to 7000 Daltons, or 350, 550, 700, 900 or 1000 to 6,000 Daltons.

Alternatively put, an alginate oligomer may have a degree of polymerisation (DP), or a number average degree of polymerisation (DPn) of 2 to 100, preferably 2 to 75, preferably 2 to 50, more preferably 2 to 40, 2 to 35, 2 to 30, 2 to 28, 2 to 25, 2 to 22, 2 to 20, 2 to 18, 2 to 17, 2 to 15 or 2 to 12.

Other representative ranges (whether for the number of residues, DP or DPn) include any one of 3, 4, 5, 6, 7, 8, 9, 10 or 11 to any one of 50, 45, 40, 39, 38, 37, 36, 35, 34, 33, 32, 31, 30, 29, 28, 27, 26, 25, 24, 23, 22, 21, 20, 19, 18, 17, 16, 15, 14, 13 or 12.

Other representative ranges (whether for the number of residues, DP or DPn) include any one of 8, 9, 10, 11, 12, 13, 14 or 15 to any one of 50, 45, 40, 39, 38, 37, 36, 35, 34, 33, 32, 31, 30, 29, 28, 27, 26, 25, 24, 23, 22, 21, 20, 19, 18, 17 or 16.

Other representative ranges (whether for the number of residues, DP or DPn) include any one of 11, 12, 13, 14, 15, 16, 17 or 18 to any one of 50, 45, 40, 39, 38, 37, 36, 35, 34, 33, 32, 31, 30, 29, 28, 27, 26, 25, 24, 23, 22, 21, 20 or 19.

An alginate oligomer will, as noted above, contain (or comprise) guluronate or guluronic acid (G) and/or mannuronate or mannuronic acid (M) residues or units. An alginate oligomer according to the invention will preferably be composed solely, or substantially solely (i.e. consist essentially of) uronate/uronic acid residues, more particularly solely or substantially solely of G and/or M residues. Alternatively expressed, in an alginate oligomer in accordance with the present invention, at least 80%, more particularly at least 85, 90, 95 or 99% of the monomer residues may be uronate/uronic acid residues, or, more particularly G and/or M residues. In other embodiments an alginate oligomer according to the invention will not comprise other residues or units (e.g. other saccharide residues, or more particularly other uronic acid/uronate residues).

References to "G residues/G" and "M residues/M" or to guluronic acid or mannuronic acid, or guluronate or mannuronate are to be read interchangeably as references to guluronic acid/guluronate and mannuronic acid/mannuronate (specifically α-L-guluronic acid/guluronate and β-D-mannuronic acid/mannuronate), and further include derivatives thereof in which one or more available side chains or groups have been modified. Common saccharide modifying groups would include acetyl, sulphate, amino, deoxy, alcohol, aldehyde, ketone, ester and anhydro groups. The alginate oligomers may also be chemically modified to add charged groups (such as carboxylated or carboxymethylated glycans) and to alter flexibility (e.g. by periodate oxidation).

Alginate oligomers may be linear, branched or cyclic.

More particularly, in a preferred embodiment at least 30% of the monomer residues of the alginate oligomer are G residues (i.e. guluronate or guluronic acid). In other words the alginate oligomer will contain at least 30% guluronate (or guluronic acid) residues. Specific embodiments thus include an alginate oligomer with (e.g. containing) 30 to 70% G (guluronate) residues or 70 to 100% G (guluronate) residues. Thus, a representative alginate oligomer according to the present invention may contain at least 70% G residues (i.e. at least 70% of the monomer residues of the alginate oligomer will be G residues).

Preferably at least 50% or 60%, more particularly at least 70% or 75%, even more particularly at least 80, 85, 90, 91, 92, 93, 94, 95, 96, 97, 98 or 99% of the monomer residues are guluronate. In one embodiment the alginate oligomer according to the invention may be an oligoguluronate (i.e. a homooligomer of G, or 100% G)

In a further embodiment, the above described alginate oligomers may have a primary structure wherein the majority of the G residues are in so called G-blocks, e.g. at least 50%, 70%, 75%, 80%, 85%, 90%, 92% or 95% of the G residues may be in G-blocks. A G block is a contiguous sequence of at least two G residues, e.g. at least 3, 4, 5 or 7 contiguous G residues.

In particular at least 90% of the G residues may be linked 1-4 to another G residue. More particularly at least 95%, 98% or 99% of the G residues of the alginate may be linked 1-4 to another G residue. This 1-4 linkage of two G residues can be alternatively expressed as a guluronic unit bound to an adjacent guluronic unit.

Suitable alginate oligomers are described in WO2007/039754, WO2007/039760, WO 2008/125828, WO2009/068841 and WO 2015/128495, the disclosures of which are explicitly incorporated by reference herein in their entirety.

In certain embodiments the alginate oligomer is an alginate oligomer of 5-20 monomer residues (which may be expressed as an alginate oligomer having a DPn of 13 or a weight average molecular weight of 3200 Da) and 90-95% of which are G residues.

It will thus be seen that a particular class of alginate oligomers according to the present invention is alginate oligomers defined as so-called "high G" or "G-block" oligomers i.e. having a high content of G residues or G-blocks (e.g. wherein at least 70% of the monomer residues are G, preferably arranged in G-blocks). However, other types of alginate oligomer may also be used are also in accordance with the invention, including in particular "high M" or "M-block" oligomers or MG-block oligomers, as described further below. Accordingly, it is alginate oligomers with high proportions of a single monomer type, and with said monomers of this type being present predominantly in contiguous sequences of that monomer type, that represent oligomers that are particularly preferred, e.g. oligomers wherein at least 70% of the monomer residues in the oligomer are G residues linked 1-4 to another G-residue, or more preferably at least 75%, and most preferably at least 80, 85, 90, 92, 93, 94, 95, 96, 97, 98, 99% of the monomers residues of the oligomer are G residues linked 1-4 to another G residue.

In other embodiments at least or, more particularly, more than 50% of the monomer residues of the alginate oligomer according to the invention may be M residues (i.e. mannuronate or mannuronic acid). In other words the alginate oligomer according to the invention may contain at least or, alternatively, more than 50% mannuronate (or mannuronic acid) residues. Specific embodiments thus include alginate oligomers with (e.g. containing) 50 to 70% M (mannuronate) residues or e.g. 70 to 100% M (mannuronate) residues. Further specific embodiments also include oligomers containing 71 to 85% M residues or 85 to 100% M residues. Thus, a representative alginate oligomer according to the present invention will contain more than 70% M residues (i.e. more than 70% of the monomer residues of the alginate oligomer will be M residues).

In other embodiments at least 50% or 60%, more particularly at least 70% or 75%, even more particularly at least 80, 85, 90, 95 or 99% of the monomer residues may be mannuronate. In one embodiment the alginate oligomer may be an oligomannuronate (i.e. a homooligomer of M, or 100% M)

In a further embodiment, the above described alginates of the invention may have a primary structure wherein the majority of the M residues are in so called M-blocks, e.g. at least 50%, 70%, 75%, 80%, 85%, 90%, 92% or 95% of the M residues are in M-blocks. An M block is a contiguous sequence of at least two M residues, e.g. at least 3, 4, 5 or 7 contiguous M residues.

In particular, at least 90% of the M residues may be linked 1-4 to another M residue. More particularly at least 95%, 98% or 99% of the M residues of the alginate are linked 1-4 to another M residue. This 1-4 linkage of two M residues can be alternatively expressed as a mannuronic unit bound to an adjacent mannuronic unit.

Other oligomers according to the invention are alginate oligomers wherein at least 70% of the monomer residues in the oligomer are M residues linked 1-4 to another M-residue, or more preferably at least 75, 80, 85, 90, 92, 93, 94, 95, 96, 97, 98, 99% of the monomers residues of the oligomer are M residues linked 1-4 to another M residue.

In a still further embodiment, alginate oligomers in accordance with the invention may comprise a sequence of alternating M and G residues. A sequence of at least three, preferably at least four, alternating M and G residues represents an MG block. The alginate oligomers of the invention may therefore comprise an MG block. Expressed more specifically, an MG block is a sequence of at least three contiguous residues consisting of G and M residues and wherein each non-terminal (internal) G residue in the contiguous sequence is linked 1-4 and 4-1 to an M residue and each non-terminal (internal) M residue in the contiguous sequence is linked 1-4 and 4-1 to a G residue.

In a further embodiment the minority uronate in the alginate oligomer (i.e. mannuronate or guluronate) may be found predominantly in MG blocks. In this embodiment at least e.g. 50%, 70%, 75%, 80%, 85%, 90% or 95% of the minority uronate monomers in the MG block alginate oligomer are present in MG blocks. In another embodiment the alginate oligomer may be arranged such that at least 50%, 60%, 70%, 80%, 85%, 90%, 95%, or 99%, e.g. 100% of the G and M residues in the oligomer are arranged in MG blocks.

An MG block containing alginate oligomer according to the invention may contain at least 1%, but less than 100%, guluronate (or guluronic acid) residues, but generally an MG block containing alginate oligomer according to the invention will contain at least 30% (or at least 35%, 40%, 45% or 50% G) but less than 100% G. Specific embodiments thus include MG block containing alginate oligomers with (e.g. containing) 1 to 30% G (guluronate) residues, 30 to 70% G (guluronate) residues or 70 to 99% G (guluronate) residues. Thus, a representative MG block containing alginate oligomer according to the present invention may contain more than 30%, but less than 70%, G residues (i.e. more than 30%, but less than 70%, of the monomer residues of the MG block alginate oligomer will be G residues).

More specifically more than 30%, more particularly more than 35%, 40%, 45%, 50%, 55%, 60% or 65%, but in each case less than 70%, of the monomer residues of the MG block containing alginate oligomer according to the invention are guluronate. Alternatively, less than 70%, more particularly less than 65%, 60%, 55%, 50%, 45%, 40% or 35%, but in each case more than 30% of the monomer residues of the MG block containing alginate oligomer according to the invention are guluronate. Any range formed by any combination of these values may be chosen. Therefore for instance the MG block containing alginate oligomer according to the invention can have e.g. between 35% and 65%, 40% and 60% or 45% and 55% G residues.

In another embodiment the MG block containing alginate oligomer according to the invention may have approximately equal amounts of G and M residues (e.g. ratios between 65% G/35% M and 35% G/65% M, for instance 60% G/40% M and 40% G/60% M; 55% G/45% M and 45% G/55% M; 53% G/47% M and 47% G/53% M; 51% G/49% M and 49% G/51% M; e.g. about 50% G and about 50% M) and these residues are arranged predominantly, preferably entirely or as completely as possible, in an alternating MG pattern (e.g. at least 50% or at least 60, 70, 80, 85, 90 or 95% or 100% of the M and G residues are in an alternating MG sequence).

References to "G residues/G" and "M residues/M" or to guluronic acid or mannuronic acid, or guluronate or mannuronate are to be read interchangeably as references to guluronic acid/guluronate and mannuronic acid/mannuronate (specifically α-L-guluronic acid/guluronate and β-D-mannuronic acid/mannuronate), and further include derivatives thereof in which one or more available side chains or groups have been modified. Common saccharide modifying groups would include acetyl, sulphate, amino, deoxy, alcohol, aldehyde, ketone, ester and anhydro groups. The alginate oligomers may also be chemically modified to add charged groups (such as carboxylated or carboxymethylated glycans), and to alter flexibility (e.g. by periodate oxidation). In other embodiments the alginate oligomer may be conjugated to another entity, e.g. another macromolecule (e.g. a protein, a peptide, a polyene, a nucleic acid, a different polysaccharide, a lipid, a vesicle forming polymer). In certain embodiments the alginate oligomer may be conjugated to an antibiotic, e.g. a polymyxin-class antibiotic (e.g. colistin) or a bacitracin.

In certain embodiments the methods of the invention may be used to determine, monitor and assess dosage regimes and/or the pharmacokinetics of alginate oligomer therapeutics. As such the invention provides a method for determining, monitoring and assessing dosage regimes and/or the pharmacokinetics of alginate oligomer therapeutics, said method comprising performing a method of the invention as defined herein on a body fluid sample from a site in or on a subject which is indicative of the dosage regime and/or the metabolism of the alginate oligomer therapeutic.

In certain embodiments the methods of the invention may comprise a subsequent step in which one or more alginate oligomers are administered to a subject or a part thereof in an amount, form and/or via an administration route which is dictated by the outcome of the above described methods. For instance, if an alginate oligomer is not detected in a body fluid sample from a region of the subject in which the alginate oligomer is intended to be, greater amounts may be subsequently administered, or subsequently administered via an alternative or additional administration route or subsequently administered to a different part of the subject. In other embodiments, the methods of the invention may be used to determine if effective amounts of an alginate oligomer are being achieved at the relevant target site. In these embodiments a sample of body fluid from the target site, or from a site which is indicative of the target site, is obtained and the level of the alginate oligomer in the sample may be determined. Depending on the levels of the alginate oligomer required at the target site, greater or lesser amounts may be administered subsequently to the subject, or administered subsequently via an alternative or additional administration route or subsequently administered to a different part of the subject.

Thus the methods of the invention may comprise a subsequent step in which one or more alginate oligomers are administered to the subject or part thereof in an amount, form or via an administration route which is different to the amount, form or administration route used on the subject prior to the method of the invention. In other embodiments the methods of the invention may comprise a subsequent step in which one or more alginate oligomers are administered to the subject or part thereof in an amount, form or via an administration route which is the same as the amount, form or administration route used on the subject prior to the method of the invention.

Thus the invention further provides a method for the treatment of a subject in need of alginate oligomer therapy, said method comprising performing one or more of the methods of the invention for detecting an alginate oligomer or for determining the concentration of an alginate oligomer in a body fluid sample as defined herein on a body fluid sample from said subject and administering an alginate oligomer to said subject or part thereof in an amount, form or via an administration route which is indicated by the results of the method of the invention for detecting an alginate oligomer or for determining the concentration of an alginate oligomer in a body fluid sample performed on the subject.

Administration of the alginate oligomer (or oligomers) to the subject, e.g. in a subsequent treatment step, may be achieved by any convenient means of administering an alginate oligomer to the subject in order to achieve effective amounts thereof in the target region of the subject, e.g. the respiratory system, the GI tract, the reproductive tract, the urinary tract, the pancreatic duct, the bile duct, the circulatory system, wounds and the sites of implanted medical devices.

Such administration may include by topical, enteral (e.g. oral, buccal, sublingual, rectal), parenteral (e.g. intravenous) routes of delivery. The subsequent distribution of the alginate oligomer may be localised or systemic. The skilled person would be able to select an appropriate administration means and body distribution to suit any particular target region or therapeutic effect and will be able to formulate alginate oligomers an into pharmaceutical compositions that are adapted for these routes of administration and body distribution according to any of the conventional methods known in the art and widely described in the literature.

More specifically, alginate oligomers may be incorporated, separately or together, optionally together with other active agents, with one or more conventional carriers, diluents and/or excipients, to produce conventional galenic preparations such as tablets, pills, granules (e.g. in free form or enclosed in capsules), powders (e.g. inhalable powders, including dry inhalable powders), lozenges, sachets, cachets, elixirs, suspensions, emulsions, solutions, syrups, aerosols (as a solid or in a liquid medium), sprays (e.g. nasal sprays), compositions for use in nebulisers, ointments, creams, salves, soft and hard gelatine capsules, suppositories, pessaries, sterile injectable solutions, sterile packaged powders, and the like. Sterile inhalable and sterile injectable compositions, especially dry inhalable powders or inhalable solutions, are of particular note.

A representative inhalable powder to be used to administer an alginate oligomer to the lower respiratory tract may contain up to 90%, e.g. up to 85%, 80%, 75% or 70%, e.g. 50 to 90%, 55 to 90%, 60 to 90%, 65 to 90%, 70 to 90%, 75 to 90%, 80 to 90%, 85 to 90%, 50 to 85%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, 75 to 80%, 50 to 70%, 55 to 70%, 60 to 70%, or 65 to 70% w/v or w/w of the oligomer, the remainder being comprised of pharmaceutically acceptable ingredients, e.g. excipients.

A representative inhalable solution to be used to administer an alginate oligomer to the upper respiratory tract typically will be sterile and may contain 6 to 25%, e.g. 6 to 20%, 6 to 15%, 6 to 10%, 8 to 25%, 8 to 20%, 8 to 15%, 9 to 25%, 9 to 20%, 9 to 15%, 10 to 15%, 10 to 20%, 10 to 25%, 15 to 20% or 15 to 25% w/v of the oligomer, the remainder being comprised of pharmaceutically acceptable ingredients, e.g. excipients, e.g. water.

For administration to the nose or paranasal sinuses a sterile aqueous and/or oil-based liquid formulation (e.g. an emulsion) may be used; administered for instance by a nasal spray device, e.g. propellant-free or propellant-assisted. A representative formulation may contain 1 to 25%, 1 to 20%, e.g. 1 to 15%, 1 to 10%, 1 to 9%, 1 to 8%, 1 to 7% or 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v or w/w of the oligomer, the remainder being comprised of pharmaceutically acceptable ingredients, e.g. excipients, e.g. water.

A representative solution for intravenous administration of an alginate oligomer to achieve systemic distribution may contain up to 1 to 25%, 1 to 20%, e.g. 1 to 15%, 1 to 10%, 1 to 9%, 1 to 8%, 1 to 7% or 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v or w/w of the alginate oligomer, the remainder being comprised of pharmaceutically acceptable ingredients, e.g. excipients, e.g. water.

A representative oral tablet to be used to administer an alginate oligomer systemically may contain up to 99%, up to 95%, 90%, 85% or 80%, e.g. 50 to 95%, 55 to 95%, 60 to 95%, 65 to 95%, 70 to 95%, 75 to 95%, 80 to 95%, 85 to 95%, 90 to 95%, 50 to 90%, 50 to 90%, 55 to 90%, 60 to 90%, 65 to 90%, 70 to 90%, 75 to 90%, 80 to 90%, 85 to 90%, 50 to 90%, 55 to 85%, 60 to 80% or, 65 to 75% w/v or w/w of the alginate oligomer, the remainder being comprised of pharmaceutically acceptable ingredients, e.g. excipients. The tablet may be a multi-layered tablet.

An enteric coated tablet may also be effective in administering an alginate oligomer to the lower GI tract. A representative enteric coated tablet may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of the oligomer, the remainder being comprised of pharmaceutically acceptable excipients, including the enteric coating (e.g. polymers including fatty acids, waxes, shellac, plastics, and plant fibres).

Enteric coated granules may also be effective in administering an alginate to the lower GI tract. Such granules may be provided in a capsule which itself may or may not be provided with an enteric coating. A representative enteric coated granule may contain up to 95%, e.g. up to 90%, 85% or 80%, e.g. 55 to 90%, 60 to 90%, 65 to 90%, 70 to 90%, 75 to 90%, 80 to 90%, 85 to 90%, 55 to 85%, 60 to 85%, 65 to 85%, 70 to 85%, 75 to 85%, 80 to 85%, 50 to 80%, 55 to 80%, 60 to 80%, 65 to 80%, 70 to 80%, or 75 to 80% w/v or w/w of the oligomer, the remainder being comprised of pharmaceutically acceptable excipients, including the enteric coating (e.g. polymers including fatty acids, waxes, shellac, plastics, and plant fibres).

A pessary may be used to administer an alginate oligomer to the lower parts of the female reproductive tract. A representative formulation may contain 1 to 25%, 1 to 20%, e.g. 1 to 15%, 1 to 10%, 1 to 9%, 1 to 8%, 1 to 7%, 1 to 6%, 5 to 25%, 5 to 20%, 5 to 15%, 5 to 10%, 5 to 9%, 5 to 8%, 5 to 7%, 5 to 6%, 8 to 25%, 8 to 20%, 8 to 15%, 8 to 10%, 9 to 25%, 9 to 20%, or 9 to 15% w/v or w/w of the oligomer, the remainder being comprised of pharmaceutically acceptable excipients, including solid excipients (e.g. paraffin and the like).

A rectal suppository may be used to administer an alginate oligomer to the lower parts of the GI tract. A representative formulation may contain 0.1 to 10%, e.g. 0.1 to 5%, 0.1 to 2%, 0.1 to 1%, 0.1 to 0.8%, 0.1 to 0.5%, 0.1 to 0.2%, 0.2 to 10%, 0.2 to 5%, 0.2 to 2%, 0.2 to 1%, 0.2 to 0.8%, 0.2 to 0.5%, 0.5 to 10%, 0.5 to 5%, 0.5 to 2%, 0.5 to 1%, 0.5 to 0.8%, 0.8 to 10%, 0.8 to 5%, 0.8 to 2%, 0.8 to 1%, 1 to 10%, 1 to 5%, 1 to 2%, 2 to 10%, 2 to 5% or 5 to 10% w/v of the alginate oligomer, the remainder being comprised of pharmaceutically acceptable excipients, including solid excipients.

"% w/v" (or "percentage weight by volume") is a commonly used expression of the concentration of a solid solute in a liquid or semi-solid solvent. 1% w/v equates to 1 gram of solid per 100 ml of solvent, 2% w/v equates to 2 g of solid per 100 ml of solvent, and so on. Accordingly local concentration may be expressed as g/100 ml, grams per 100 millilitres, g100 ml−1. 1% w/v also equates to 10 gram of solid per litre of solvent. Likewise, "% w/w" (or "percentage weight by weight") is a commonly used expression of the amount of a compound in a solid. 1% w/w equates to 1 gram of compound per 100 g of solid, 2% w/w equates to 2 g of compound per 100 g of solid, and so on. Accordingly, % w/w may be expressed as g/100 g, grams per 100 grams and g 100 $g^{-1}$. 1% w/w also equates to 10 gram of compound per kilogram of solid. The skilled person would understand that through appropriate scaling calculations, the local concentration range of the present range can be expressed in terms of any SI unit of mass and volume. Conversion into non-standard measures of concentration is also possible and would be routine to the skilled man.

The invention will be further described with reference to the following non-limiting Examples in which FIG. 1 shows second derivative FTIR absorbance spectra ($1200\ cm^{-1}$ to $950\ cm^{-1}$) for patient 20801001 at visit 4 (V4, placebo) and visit 7 (V7, treatment) aligned to second derivative OligoG spectrum ($1200\ cm^{-1}$ to $950\ cm^{-1}$). The top image shows second derivative spectra for OligoG treated (solid line) and placebo treated (dashed line) phases. The bottom image shows the second derivative spectrum for OligoG with good correspondence of peaks to the treated spectrum in the top image.

FIG. 2 shows the distribution of correlation coefficients between raw, processed FTIR absorbance spectra for patient samples and raw, processed FTIR absorbance spectra for OligoG. Screening samples (downwards left to right diagonal); placebo samples (hatched); OligoG treated samples (upwards left to right diagonal).

FIG. 3 shows the distribution of correlation coefficients between second derivative FTIR absorbance spectra for patient samples and between second derivative FTIR absorbance spectra for OligoG. Screening samples (downwards left to right diagonal); placebo samples (hatched); OligoG treated samples (upwards left to right diagonal).

FIG. 4 shows a scatterplot of all correlation coefficients between sputum sample and OligoG for raw as well as second derivative FTIR absorbance spectra simultaneously. The black line optimally separates samples from treatment phase (black diamonds) from samples from placebo or screening/day 0 phases (white diamonds and white circles, respectively) and gives rise to the linear prediction model of the invention that predicts the presence or absence of OligoG (Y=−1.9643X+1.7286).

FIG. 5 shows vector-normalised, baseline corrected FTIR absorbance spectra from 1800-900 $cm^{-1}$ for OligoG (grey), control CF sputum (black), and OligoG-incubated CF sputum in progressively increasing concentrations from 0.02% to 20% (short dash 0.02%; long dash single dot 0.05%; medium dash 0.1%; long dash double dot 0.2%, dotted 0.5%; long dash 1.0%; medium dash double dot 1.5%; extra-long dash 2.0%).

FIG. 6 shows vector-normalised, baseline corrected FTIR absorbance spectra from 1200-900 $cm^{-1}$ for OligoG (grey), control CF sputum (black), and OligoG-incubated CF sputum in progressively increasing concentrations from 0.02% to 20% (short dash 0.02%; long dash single dot 0.05%; medium dash 0.1%; long dash double dot 0.2%, dotted 0.5%; long dash 1.0%; medium dash double dot 1.5%; extra-long dash 2.0%).

FIG. 7 shows second derivative FTIR absorbance spectra from 1200-900 $cm^{-1}$ for OligoG (grey), control CF sputum (black), and OligoG-incubated CF sputum in progressively increasing concentrations from 0.02% to 20% (short dash 0.02%; long dash single dot 0.05%; medium dash 0.1%; long dash double dot 0.2%, dotted 0.5%; long dash 1.0%; medium dash double dot 1.5%; extra-long dash 2.0%).

Figure 16:
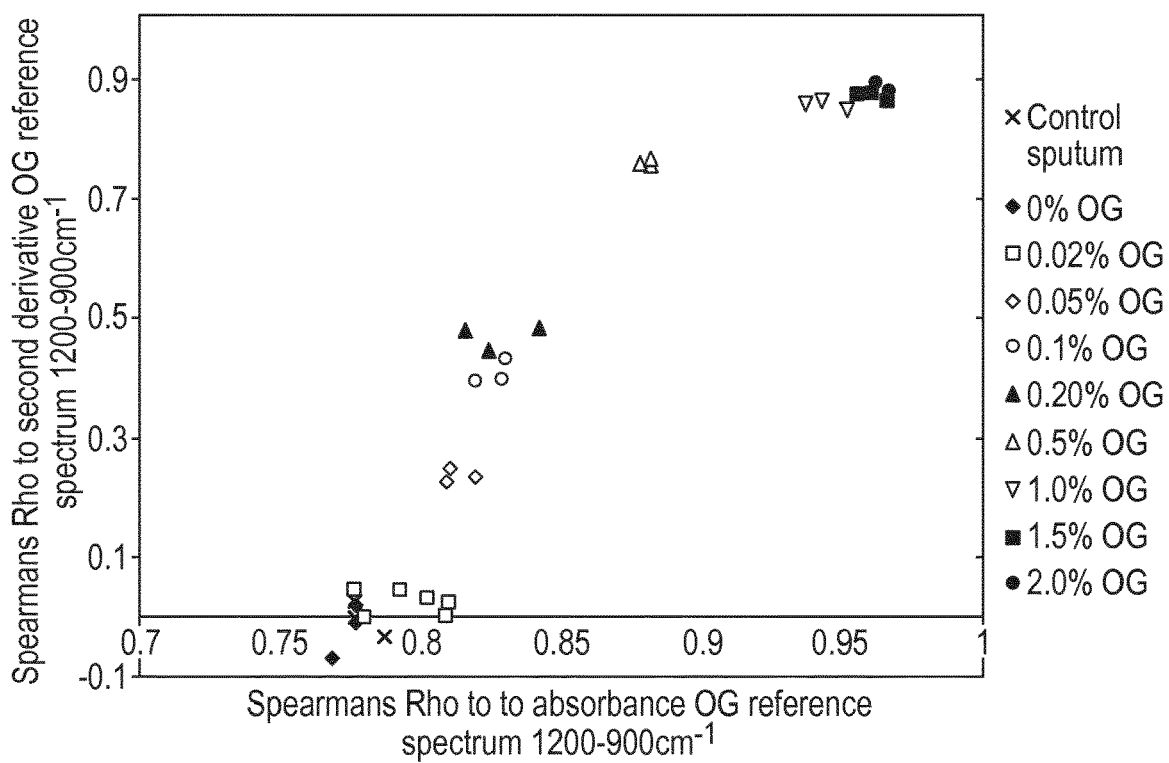

FIG. 16 shows Spearman's Rho values for correlations between the second derivative FTIR absorbance spectra at wavenumbers 1200-900 $cm^{-1}$ for CF sputum samples of increasing OligoG concentration and the second derivative FTIR absorbance spectra at wavenumbers 1200-900 $cm^{-1}$ for OligoG plotted over Spearman's Rho values for correlations between the raw FTIR absorbance spectra at wavenumbers 1200-900 $cm^{-1}$ for CF sputum samples of increasing OligoG concentration and the raw FTIR absorbance spectra at wavenumbers 1200-900 $cm^{-1}$ for OligoG. Control sputum (X); 0% OligoG (black diamond); 0.02% OligoG (white square); 0.05% OligoG (white diamond); 0.1% OligoG (circle); 0.2% OligoG (black triangle), 0.5% OligoG (white triangle); 1.0% OligoG (inverted triangle); 1.5% OligoG (black square); 2.0% OligoG (black circle). The data points cluster according to OligoG concentration.

EXAMPLES

Example 1—Detection of OligoG by FTIR in Sputum of Cystic Fibrosis Patients

Fourier Transform Infrared Spectroscopy (FTIR)

IR spectra were obtained with a Bruker Vertex Fourier Transform IR (FTIR) instrument equipped with a high-throughput system (HTS) module (Bruker Optics). FTIR transmission mode was used for spectral generation. For all samples, 3 µL of sputum was carefully spotted directly onto a 96-well silicon plate using a pipette tip to ensure that the entire volume covered spot with no spillage. Each sample was slowly evaporated at room temperature. Infrared spectra were collected as an average of 24 scans per sample between the wavenumber range of 4000-450 $cm^{-1}$ at a resolution of 4 $cm^{-1}$, controlled by Optics User Software (OPUS) version 7.0 (Bruker Optics). The process was repeated until six replicates of set reproducibility were generated per sample. An infrared spectrum was generated for an alginate oligomer of DP 5 to 20 (weight average molecular weight 3200 Da) and 90-95% G residues (OligoG) by following the same procedure with an 0.2% (w/v) solution of the oligomer in distilled water.

Prior to the acquisition of each sample spectrum, the silicon plates were thoroughly cleaned using isopropyl alcohol in de-ionized water and dried. A background spectrum was automatically measured for each sample using 24 scans and subtracted from the sample spectrum acquired immediately after.

Data Processing

The resulting sputum spectra were pre-processed using OPUS software version 7 (Bruker Optics) by subtracting a baseline between 1800 and 950 $cm^{-1}$. The level of reproducibility among the six replicates within each sample was calculated for the 1800-950 $cm^{-1}$ region using the spectral distance (D), a dissimilarity measure, where: D is equal to $(1-r) \times 1000$ and r is Pearson's correlation coefficient. A spectrum having a D value greater than 10 when compared to any another spectrum would be considered an inadequate replicate and rejected. All spectral comparisons had a D value less than 10 showing high reproducibility. An average spectrum was then calculated for each sample based on the six replicates. Average spectra were normalized using vector normalization. This had the effect of absorbance at the Amide 1 peak at approximately 1640 $cm^{-1}$ to be equal across spectra allowing all spectra to be compared. Second derivative spectra were calculated for all processed raw spectra using the OPUS software with 9 point Savitzky-Golay smoothing.

Statistical Analysis

All data analysis was performed using the R Statistical Programming Environment. Correlation analysis was applied to sputum raw or second derivative spectra and OligoG spectra using Spearman's correlation within the 'cor.test'. All data were initially assessed for normality using the Shapiro-Wilk test.

Patients

Sputum samples from 15 patients involved in a phase IIb trial involving OligoG were obtained. All patients included a sample at screening/day 0 (pre-treatment/pre-placebo) and at least one sample during placebo or OligoG treatment phase.

Infrared Spectral Data

Visit dependent variation in infrared absorbance was observed at various regions across the spectra for all patients. It was also seen that OligoG absorbs strongly between infrared wave numbers 1200 cm$^{-1}$ and 950 cm$^{-1}$ and so it was decided to assess this region further for OligoG detection during treatment phase. We refer to this region of the spectrum hereafter as the 'OligoG region'.

Figure 1:
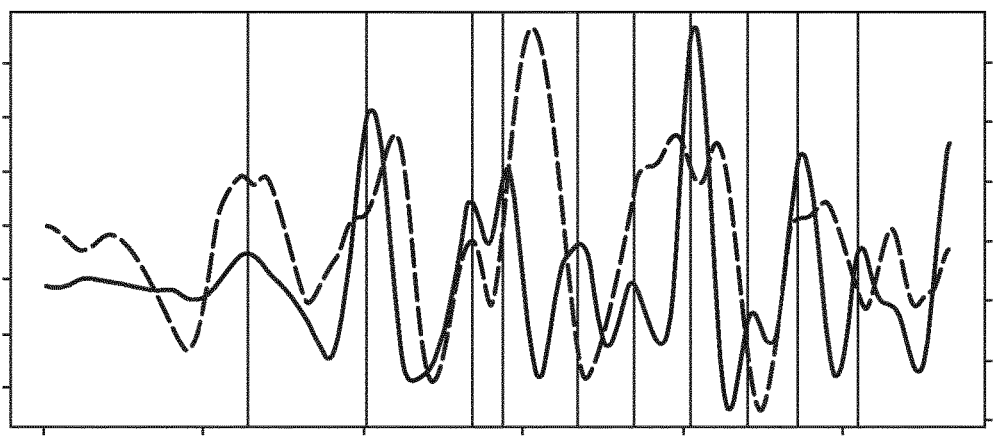
Figure 1:
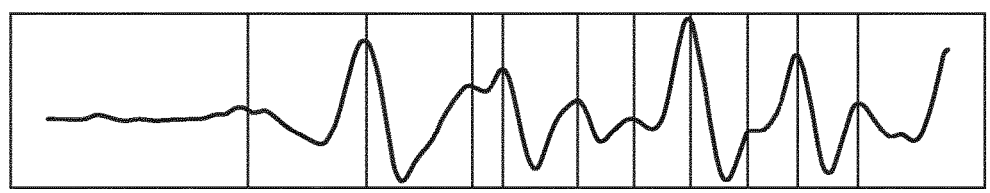

Examples of second derivative infrared spectral data within the OligoG region for patient 20801001 as well as an OligoG standard infrared spectrum is shown in FIG. 1. Graphical analysis of treated phase spectra aligned with OligoG spectra showed that OligoG peaks could be detected by eye.

To maximise the ability to differentiate a treatment spectrum from a placebo or untreated spectrum (i.e. determine if OligoG was present in a sample) it was decided to apply correlation analysis to both raw and second derivative spectra and use the correlation coefficients in a two dimensional Cartesian plot to separate samples according to how similar their infrared profiles were to a standard OligoG spectrum. This two-dimensional 'map' of similarity could then be used to develop a simple linear model that could predict if a sample contained OligoG or not.

Correlation Analysis of Treated and Untreated Spectra.

Within the 'OligoG region', we compared each sample spectrum with the OligoG standard spectrum for both raw absorbance spectra and second derivative spectra. We calculated Spearman's correlation coefficients in each case which showed a degree of similarity between 0 and 1 (where a coefficient of 1 would mean identical). Both sets of correlation coefficients for each sample are shown in columns 5 and 6 in Table 1.

| 1 Patient ID | 2 Visit No. | 3 Sample ID | 4 Treatment Phase | 5 Abs Spearman's Rho | 6 2D Spearman's Rho | 7 OligoG Predicted? | 8 Correct? 2A | 9 Correct? 2B* |
|---|---|---|---|---|---|---|---|---|
| 20801001 | V2 | AP103 | Screening/Day 0 | 0.85 | 0.09 | Y | N | Y |
| 20801001 | V3 | AP105 | Placebo | 0.81 | 0.11 | N | Y | Y |
| 20801001 | V4 | AP114 | Placebo | 0.84 | 0.05 | N | Y | Y |
| 20801001 | V5 | AP127 | Wash out | 0.90 | 0.86 | Y | N | N |
| 20801001 | V7 | AP148 | Treated | 0.93 | 0.90 | Y | Y | Y |
| 20801001 | V7 | AP149 | Treated | 0.88 | 0.82 | Y | Y | Y |
| 20801001 | V7 | AP148 + 149 | Treated | 0.92 | 0.88 | Y | Y | Y |
| 27601001 | V2 | AP112 | Screening/Day 0 | 0.79 | 0.09 | N | Y | Y |
| 27601001 | V3 | AP120 | Placebo | 0.80 | 0.09 | N | Y | Y |
| 27601001 | V4 | AP123 | Placebo | 0.80 | 0.07 | N | Y | Y |
| 27601001 | V5 | AP140 | Washout | 0.80 | 0.07 | N | Y | Y |
| 27601001 | V6 | AP154 | Treated | 0.82 | 0.40 | Y | Y | Y |
| 27601001 | V7 | AP170 | Treated | 0.82 | 0.14 | Y | Y | Y |
| 27601002 | V2 | AP116 | Screening/Day 0 | 0.83 | 0.02 | N | Y | Y |
| 27601002 | V3 | AP119 | Treated | 0.84 | 0.30 | Y | Y | Y |
| 27601002 | V4 | AP122 | Treated | 0.80 | 0.25 | Y | Y | Y |
| 27601002 | V6 | AP155 | Placebo | 0.85 | 0.11 | Y | N | Y |
| 27601002 | V7 | AP171 | Placebo | 0.79 | 0.05 | N | Y | Y |
| 27605001 | V1 | AP190 | Screening/Day 0 | 0.81 | 0.08 | N | Y | Y |
| 27605001 | V2 | AP200 | Screening/Day 0 | 0.83 | 0.00 | N | Y | Y |
| 27605001 | V3 | AP219 | Placebo | 0.85 | 0.02 | N | Y | Y |
| 27605001 | V4 | AP233 | Placebo | 0.78 | 0.09 | N | Y | Y |
| 27605001 | V6 | AP271 | Treated | 0.86 | 0.04 | Y | Y | Y |
| 27605001 | V7 | AP292 | Treated | 0.84 | 0.18 | Y | Y | Y |
| 27606002 | V1 | AP178 | Screening/Day 0 | 0.79 | 0.10 | N | Y | Y |
| 27606002 | V3 | AP192 | Placebo | 0.78 | 0.15 | N | Y | Y |
| 27606002 | V4 | AP202 | Placebo | 0.77 | 0.04 | N | Y | Y |
| 27606002 | V6 | AP263 | Treated | 0.81 | 0.18 | Y | Y | Y |
| 27606002 | V7 | AP287 | Treated | 0.81 | 0.09 | N | N | N |
| 27606004 | V1 | AP203 | Screening/Day 0 | 0.86 | 0.24 | Y | N | Y |
| 27606004 | V2 | AP217 | Screening/Day 0 | 0.85 | 0.07 | Y | N | Y |
| 27606004 | V3 | AP235 | Placebo | 0.80 | 0.07 | N | Y | Y |
| 27606004 | V4 | AP248 | Placebo | 0.80 | 0.06 | N | Y | Y |
| 27606004 | V6 | AP303 | Treated | 0.92 | 0.89 | Y | Y | Y |
| 27606004 | V7 | AP330 | Treated | 0.80 | 0.31 | Y | Y | Y |
| 27606005 | V1 | AP218 | Screening/Day 0 | 0.68 | 0.03 | N | Y | Y |
| 27606005 | V3 | AP247 | Treated | 0.80 | 0.35 | Y | Y | Y |
| 27606005 | V4 | AP262 | Treated | 0.82 | 0.12 | Y | Y | Y |
| 27606005 | V6 | AP312 | Placebo | 0.81 | 0.06 | N | Y | Y |
| 27606005 | V7 | AP337 | Placebo | 0.85 | 0.10 | Y | N | N |
| 27607001 | V1 | AP229 | Screening/Day 0 | 0.79 | 0.06 | N | Y | Y |
| 27607001 | V3 | AP245 | Placebo | 0.84 | 0.09 | Y | N | N |
| 27607001 | V4 | AP266 | Placebo | 0.86 | 0.01 | N | Y | Y |
| 27607001 | V7 | AP339 | Treated | 0.85 | 0.38 | Y | Y | Y |
| 75201001 | V1 | AP104 | Screening/Day 0 | 0.84 | 0.08 | Y | N | Y |
| 75201001 | V2 | AP110 | Screening/Day 0 | 0.81 | 0.08 | N | Y | Y |
| 75201001 | V3 | AP117 | Treated | 0.86 | 0.39 | Y | Y | Y |
| 75201001 | V4 | AP121 | Treated | 0.88 | 0.57 | Y | Y | Y |
| 75201001 | V6 | AP150 | Placebo | 0.84 | 0.09 | Y | N | Y |

-continued

| 1 Patient ID | 2 Visit No. | 3 Sample ID | 4 Treatment Phase | 5 Abs Spearman's Rho | 6 2D Spearman's Rho | 7 OligoG Predicted? | 8 Correct? 2A | 9 Correct? 2B* |
|---|---|---|---|---|---|---|---|---|
| 75201001 | V7 | AP161 | Placebo | 0.84 | 0.12 | Y | N | N |
| 82603001 | V1 | AP164 | Screening/Day 0 | 0.83 | 0.09 | N | Y | Y |
| 82603001 | V2 | AP165 | Screening/Day 0 | 0.81 | 0.09 | N | Y | Y |
| 82603001 | V3 | AP166 | Placebo | 0.84 | 0.01 | N | Y | Y |
| 82603001 | V4 | AP205 | Placebo | 0.85 | 0.08 | Y | N | N |
| 82603001 | V6 | AP227 | Treated | 0.86 | 0.13 | Y | Y | Y |
| 82603001 | V7 | AP242 | Treated | 0.85 | 0.07 | Y | Y | Y |
| 82603002 | V1 | AP201 | Screening/Day 0 | 0.16 | 0.05 | N | Y | Y |
| 82603002 | V2 | AP226 | Screening/Day 0 | 0.82 | 0.05 | N | Y | Y |
| 82603002 | V3 | AP241 | Treated | 0.83 | 0.11 | Y | Y | Y |
| 82603002 | V4 | AP267 | Treated | 0.83 | 0.07 | N | N | N |
| 82603002 | V6 | AP332 | Placebo | 0.84 | 0.09 | N | Y | Y |
| 82604004 | V1 | AP230 | Screening/Day 0 | 0.88 | 0.78 | Y | N | Y |
| 82604004 | V2 | AP261 | Screening/Day 0 | 0.83 | 0.07 | N | Y | Y |
| 82604004 | V4 | AP307 | Placebo | 0.86 | 0.00 | N | Y | Y |
| 82604004 | V6 | AP354 | Treated | 0.85 | 0.63 | Y | Y | Y |
| 82604004 | V7 | AP381 | Treated | 0.86 | −0.07 | N | N | N |
| 82606001 | V1 | AP199 | Screening/Day 0 | 0.84 | 0.09 | Y | N | Y |
| 82606001 | V2 | AP222 | Screening/Day 0 | 0.88 | 0.79 | Y | N | Y |
| 82606001 | V3 | AP221 | Treated | 0.86 | 0.05 | Y | Y | Y |
| 82606001 | V6 | AP294 | Placebo | 0.85 | 0.06 | N | Y | Y |
| 82606001 | V7 | AP300 | Placebo | 0.84 | 0.07 | N | Y | Y |
| 82606003 | V1 | AP274 | Screening/Day 0 | 0.84 | 0.09 | Y | N | Y |
| 82606003 | V2 | AP295 | Screening/Day 0 | 0.83 | 0.10 | N | Y | Y |
| 82606003 | V3 | AP323 | Placebo | 0.86 | 0.01 | N | Y | Y |
| 82606003 | V4 | AP336 | Placebo | 0.85 | 0.07 | Y | N | N |
| 82606003 | V6 | AP390 | Treated | 0.84 | 0.55 | Y | Y | Y |
| 82606003 | V7 | AP401 | Treated | 0.86 | 0.66 | Y | Y | Y |
| 82606004 | V2 | AP301 | Screening/Day 0 | 0.79 | 0.12 | N | Y | Y |
| 82606004 | V3 | AP319 | Treated | 0.85 | 0.48 | Y | Y | Y |
| 82606004 | V4 | AP350 | Treated | 0.81 | 0.08 | N | N | N |
| 82606004 | V6 | AP392 | Placebo | 0.80 | 0.07 | N | Y | Y |

*revised predictions based on influence of test inhalation at screening and potential carry-over of OligoG from first treatment period.

Figure 2:
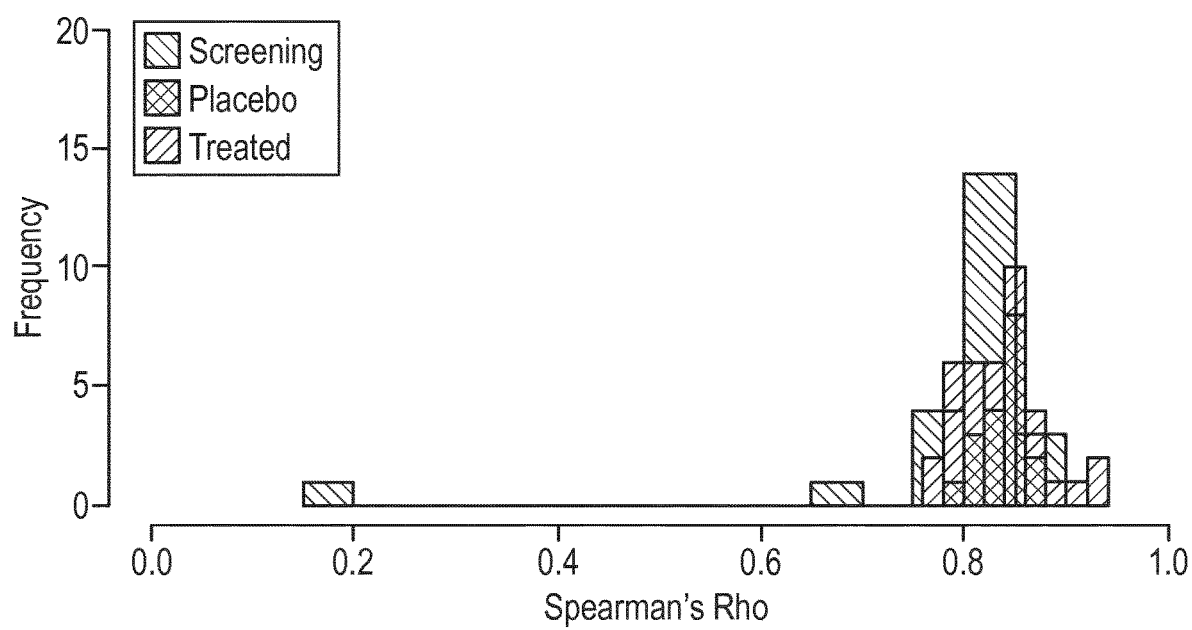
Figure 3:
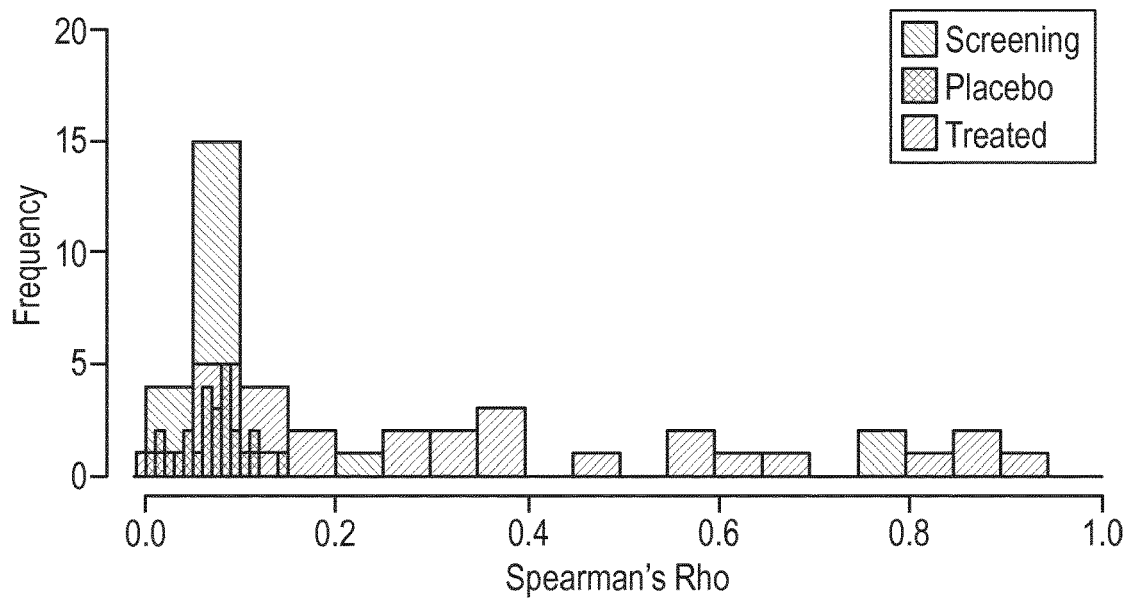

The distributions of the Spearman's Rho coefficients for samples at treated, placebo and screening phases are shown for raw (FIG. 2) and second derivative (FIG. 3) spectra. It is clear that the second derivative spectra are much more discriminatory between phases.

For each sample, scatter plots for the raw versus second derivative spectra correlation coefficients were constructed to visualise how the treated phase samples compared to the placebo phase and screening/day 0 samples. These scatter-plots represents 'maps' of how similar or different the sample spectra are to a standard OligoG spectrum. It was generally observed that the second derivative spectra from treatment samples had higher correlation than raw spectra but both might be useful to generate a predictive model.

Figure 4:
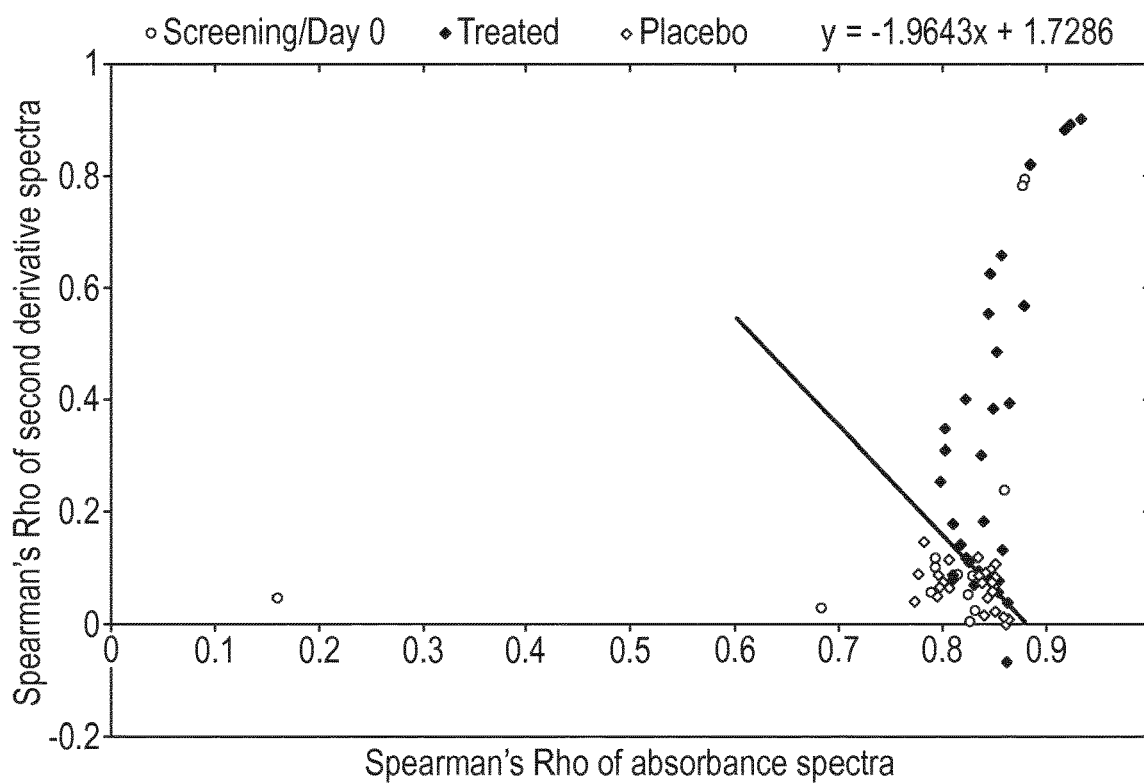

To develop a predictive model, a single scatter plot was generated to show all correlation coefficients from Table 1 mapped simultaneously (FIG. 4). A linear model was then developed to optimise the separation of treated and placebo samples, using both raw and second derivative correlation coefficients. Visually, the model is represented as a line in FIG. 4. Any point on or above the line is predicted as being a sample containing OligoG and any point below the line is predicted as not containing OligoG. The model is based on the following formula:

$$Y = -1.9643X + 1.7286$$

Therefore, for any sample, to predict if OligoG is present, the correlation coefficient between the raw absorbance spectrum and OligoG standard is inputted as 'X' into the equation. The resulting 'Y' value is then used to determine if OligoG is present. If the sample's correlation coefficient between the second derivative spectrum and OligoG standard spectrum is greater than or equal to the predicted Y the model predicts OligoG is present.

The sensitivity and specificity for the model were then determined by inputting the absorbance spectra correlation coefficients (column 5 in Table 1) into the equation for each sample. Predicted Y values were then compared to the second derivative correlation coefficients (column 6 in Table 1) and checked if the prediction was correct or not.

The prediction in each case is shown in column 7 in Table 1 and the accuracy of prediction in column 8. Those cases where the model incorrectly predicted that OligoG was not present were always for the second treatment visit in the time series.

Table 2A shows the sensitivity and specificity of the prediction model. The sensitivity of detecting OligoG was 0.86 whereas the overall specificity of the model (i.e. determining that OligoG was not present) was 0.70. The sensitivity as calculated using just placebo samples was 0.74. However, when allowance is made for the OligoG test inhalation in all subjects at screening, combined with the carry-over effects of OligoG when administered in the first treatment period, the overall test specificity increased to 0.90 (Table 2B).

TABLE 2A

Sensitivity and specificity calculations for the OligoG predictive model. The table shows a breakdown of samples accurately predicted to contain or not contain OligoG according to whether the samples were taken at treatment, placebo or Screening/Day 0 phase (or time point). The placebo or Screening/Day 0 phase predictions were also combined for an overall estimate of specificity.

|  | Treated | Placebo | Screening/Day 0 | Placebo & Screening/Day 0 |
|---|---|---|---|---|
| Total Samples | 29 | 27 | 23 | 50 |
| Correctly Predicted | 25 | 20 | 15 | 35 |
| Incorrectly Predicted | 4 | 7 | 8 | 15 |
| Sensitivity | 0.86 | | | |
| Specificity | | 0.74 | 0.65 | 0.70 |

TABLE 2B

Revised sensitivity and specificity calculations based on the revised predictions (Table 1, "Correct? 2B") in view of influence of test inhalation at screening and potential carry-over of OligoG from first treatment period. The placebo or Screening/Day 0 phase predictions were also combined for an overall estimate of specificity.

|  | Treated | Placebo | Screening/Day 0 | Placebo & Screening/Day 0 |
|---|---|---|---|---|
| Total Samples | 29 | 27 | 23 | 50 |
| Correctly Predicted | 25 | 22 | 23 | 45 |
| Incorrectly Predicted | 4 | 5 | 0 | 5 |
| Sensitivity | 0.86 | | | |
| Specificity | | 0.81 | 1.0 | 0.90 |

Discussion

The results of this study show that FTIR was able to identify alginate oligomers (OligoG) in sputum from cystic fibrosis patients. At its simplest this may be by comparing a second derivative FTIR spectrum of a test sample with a second derivative FTIR spectrum of the alginate oligomer. Alginate oligomers can also be detected by simply calculating the correlations between raw and second derivative FTIR absorbance spectra for a test sample and an alginate oligomer standard and applying said coefficients to a simple linear formula. The procedure is simple and rapid and all data are generated from a single sample and a reference alginate spectrum in a library. The method is non-invasive, reproducible and cost-effective per sample.

The calculated sensitivity value for the proposed prediction model suggests that 80% of samples tested would correctly show if an alginate oligomer spectrum is present. However, some notable exceptions suggest that the sensitivity and specificity could be significantly higher: the high rate of apparently false positive predictions for the V2 screening samples is likely due to patients having already received a single dose of alginate oligomer as a test inhalation at the V2 screening visit. Although not all screening samples showed presence of OligoG this may have been due to how effective the test inhalation was and whether the sputum sample was taken before or after the inhalation. In addition, the wider clinical findings of the clinical trial also indicated that the OligoG effects are sustained well after the cessation of OligoG treatment, suggesting that OligoG may still be present in the sputum and sputum plugs yet to be expectorated. That OligoG could still be present in the sputum at the end of the wash-out period would therefore result in a true positive detection for OligoG in those V6 samples at the start of the placebo period. Taking these effects into consideration, it is likely that the true specificity exceeds 80%.

Additional factors influencing the detection of OligoG, include patient compliance (ie., patients not inhaling medication correctly or missing doses), interference from other 'foreign' molecules (e.g. food) providing dominant infrared peaks in the spectrum that could lower the correlation between sample and OligoG standard. False positive results might also occur due to 'foreign' conflicting sugars in sputum that yield a similar infrared profile to OligoG.

Example 2—Determining the Concentration of OligoG in Sputum of Cystic Fibrosis Patients by FTIR The aim of this experiment was to incubate a CF-patient sputum sample with increasing concentrations of OligoG with the objective of measuring absorbance at OligoG-specific wavenumbers. Standard curves of absorption at each OligoG-specific wavenumber were then calculated. Correlation analysis between each spectrum and a reference OligoG spectrum was also performed. Standard curves of absorption and correlation are shown below with polynomial trendlines showing $R^2$ values in excess of 0.95, indicating that FTIR analysis is capable of accurately estimating OligoG concentration in sputum.

Method

OligoG stock solutions from 0% w/v up to 20% w/v were prepared for incubation with CF-patient sputum at a 1:10 (OG:Sputum) dilution. Table 1 shows all the stock concentrations and final OG in sputum concentrations. OG was incubated with sputum at 37° C. for 30 minutes.

TABLE 3

OligoG stock solution concentrations and final concentration of OligoG in sputum after incubation

| Stock conc. OligoG (% w/v) | Dilution factor (OligoG:Sputum) | Final OligoG conc. in Sputum (% w/v) |
|---|---|---|
| 0 | 1:10 | 0 |
| 0.2 | | 0.02 |
| 0.5 | | 0.05 |
| 1 | | 0.1 |
| 2 | | 0.2 |
| 5 | | 0.5 |
| 10 | | 1 |
| 15 | | 1.5 |
| 20 | | 2 |

FTIR analysis was performed, as described in Example 1, on the incubated CF sputum samples, and non-incubated CF sputum was used as a control sample. Replicate spectra (n=3) were acquired using the Bruker Alpha ATR-FTIR spectrometer. Spectra were processed using the in-built OPUS spectral processing tools for normalization, baseline correction, and second derivative calculation.

Absorption Curves

OligoG-incubated sputum IR-spectra were generated and the absorption at peak positions corresponding to major OligoG absorption peaks were plotted against the corresponding concentration of OligoG in sputum (FIGS. 8-13). Table 4 shows the wavenumbers of interest which were examined.

TABLE 4

Oligo G absorption peak positions, intensities and widths

| Peak Positon | Absorption Intensity | Width |
|---|---|---|
| 1601.522 | 0.417 | 55.0644 |
| 1412.537 | 0.256 | 36.4529 |
| 1124.84 | 0.187 | 13.1034 |
| 1086.016 | 0.272 | 19.9577 |
| 1028.324 | 0.374 | 35.0735 |
| 949.3862 | 0.129 | 19.5884 |

Correlation Analysis

Each IR-spectrum of OligoG-incubated and control CF-sputum was correlated to a reference OligoG spectrum using a non-parametric correlation test (Spearman's). Both absorbance and second derivative spectra were correlated to the corresponding OligoG absorbance or second derivative spectrum. The most distinct peaks found in the OligoG spectrum are found within the glycogen-rich region from 1200-900 cm$^{-1}$. For this reason, the correlation analysis was focused within this region.

Results and Discussion

Figure 5:
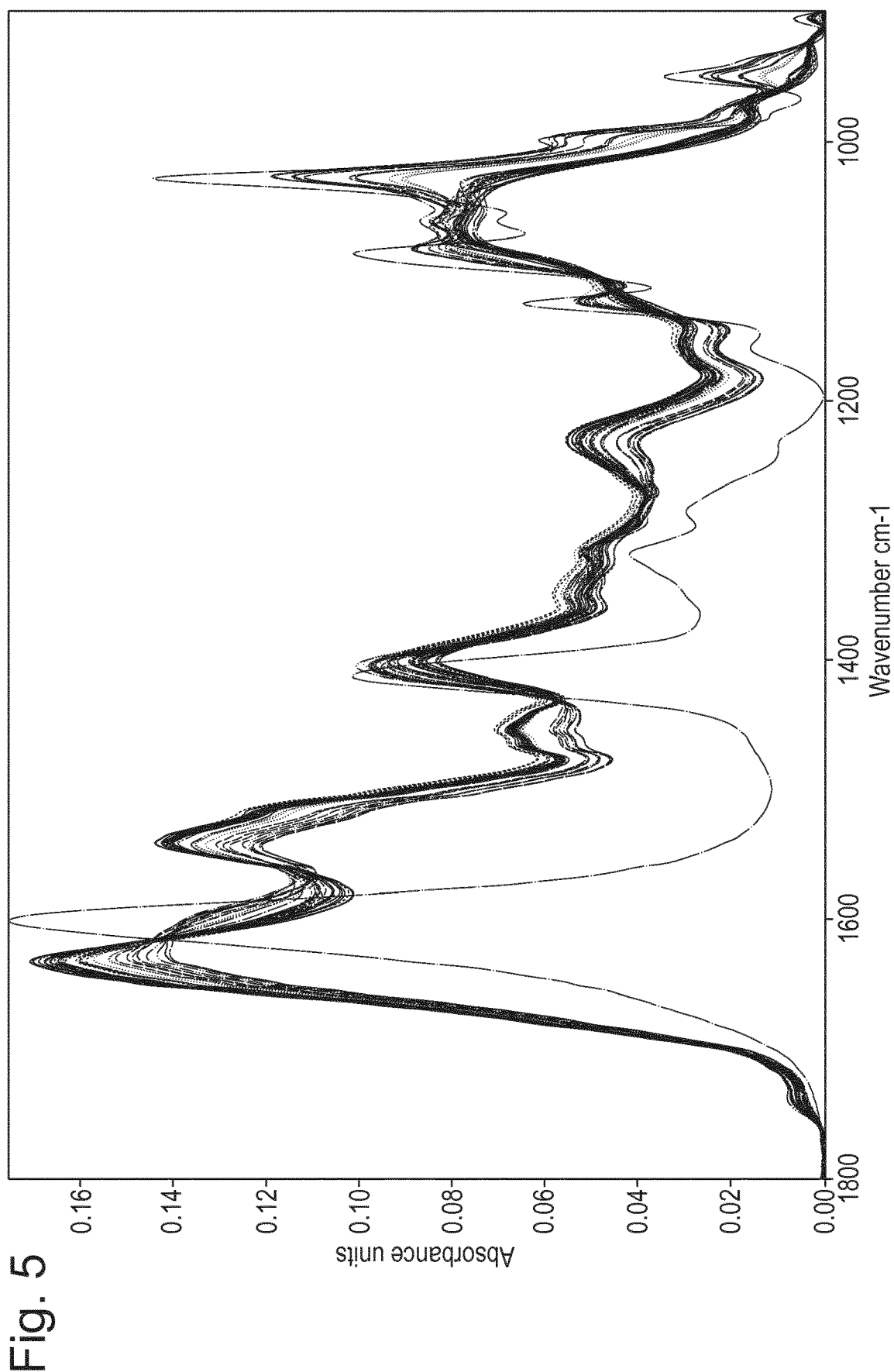
Figure 6:
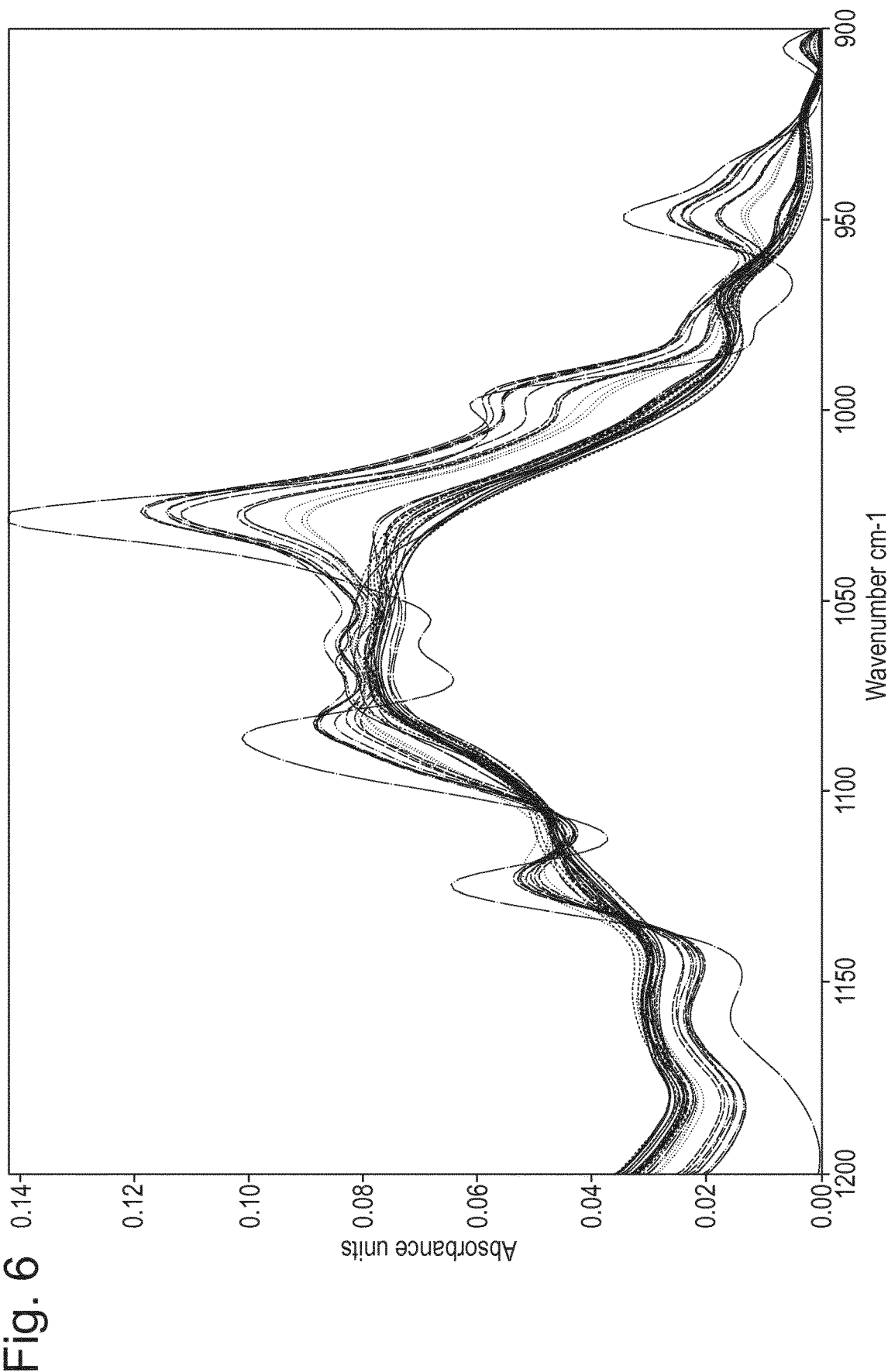
Figure 7:
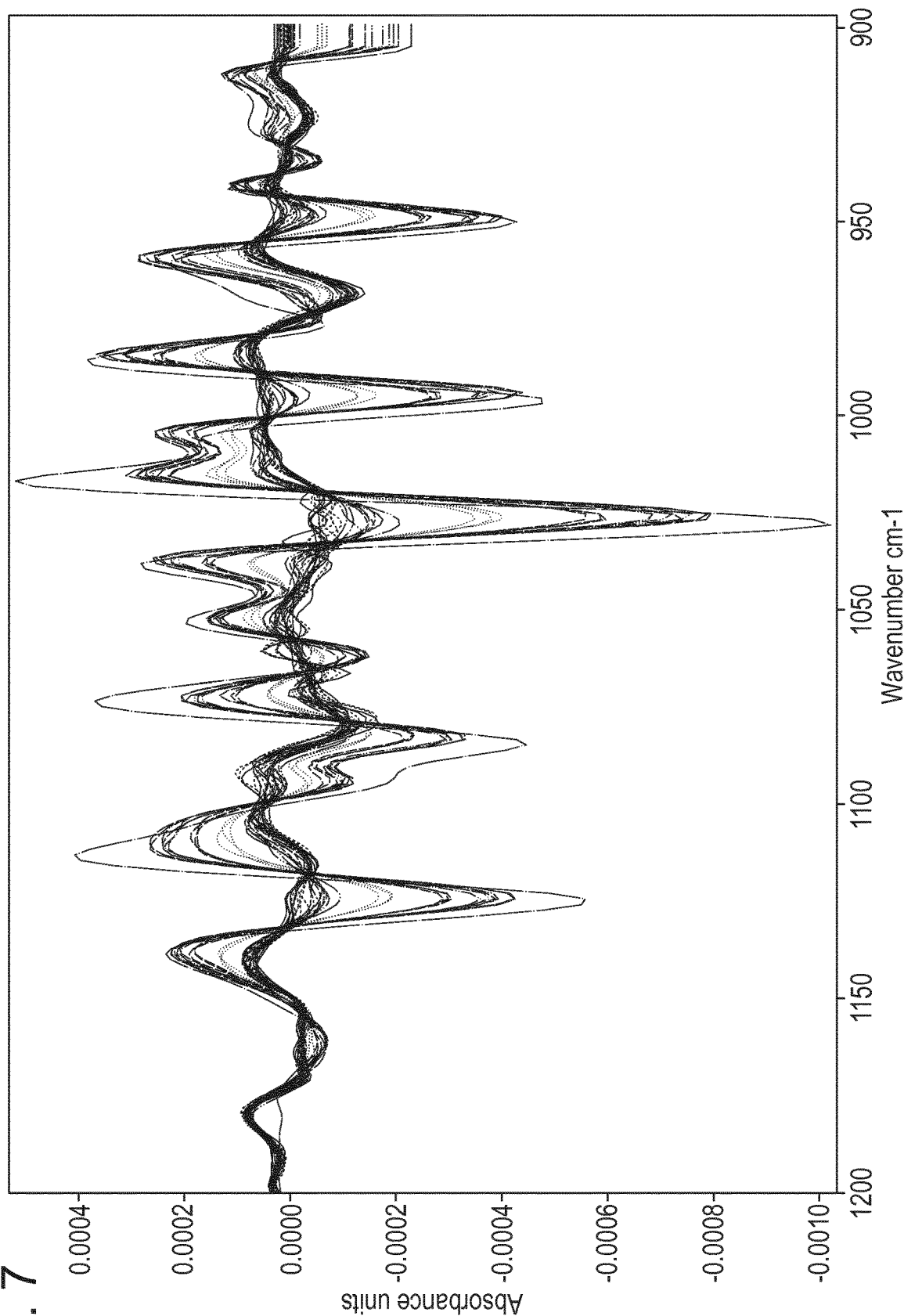
Figure 8:
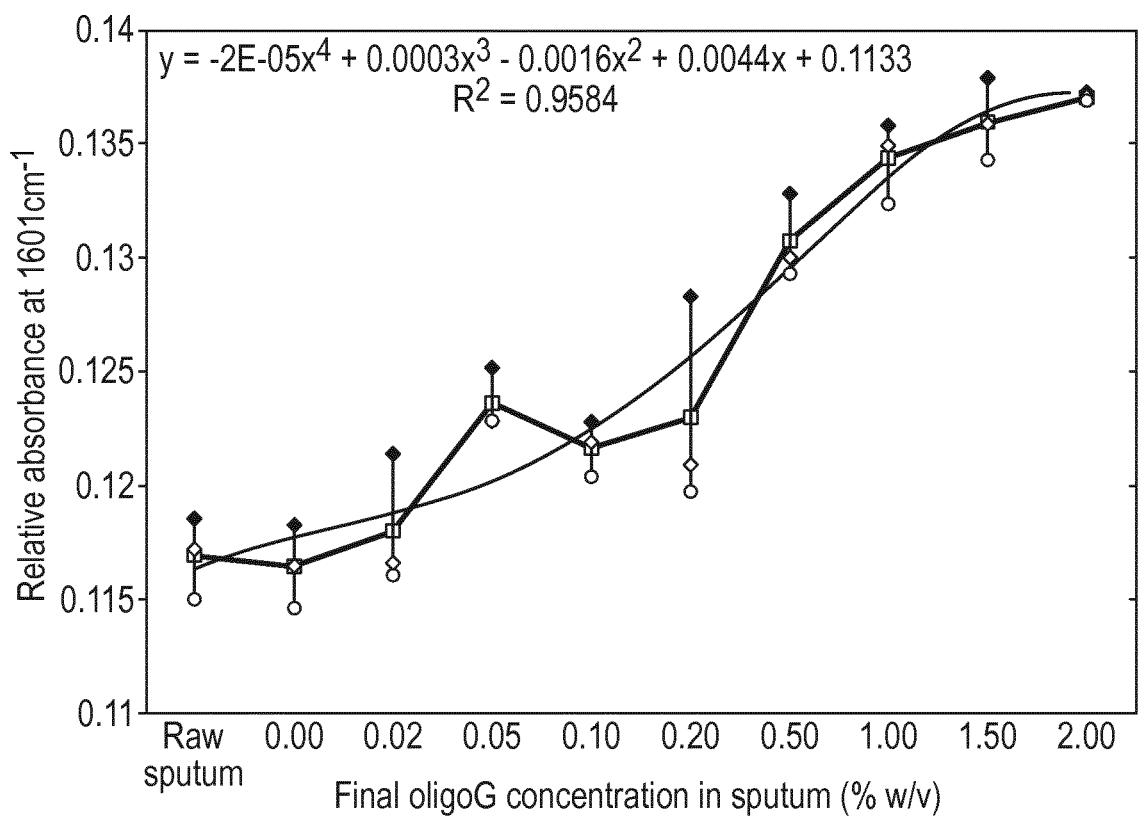
FIG. 8 shows FTIR absorbance values at 1601 $cm^{-1}$ for CF sputum samples of increasing OligoG concentration.
Figure 9:
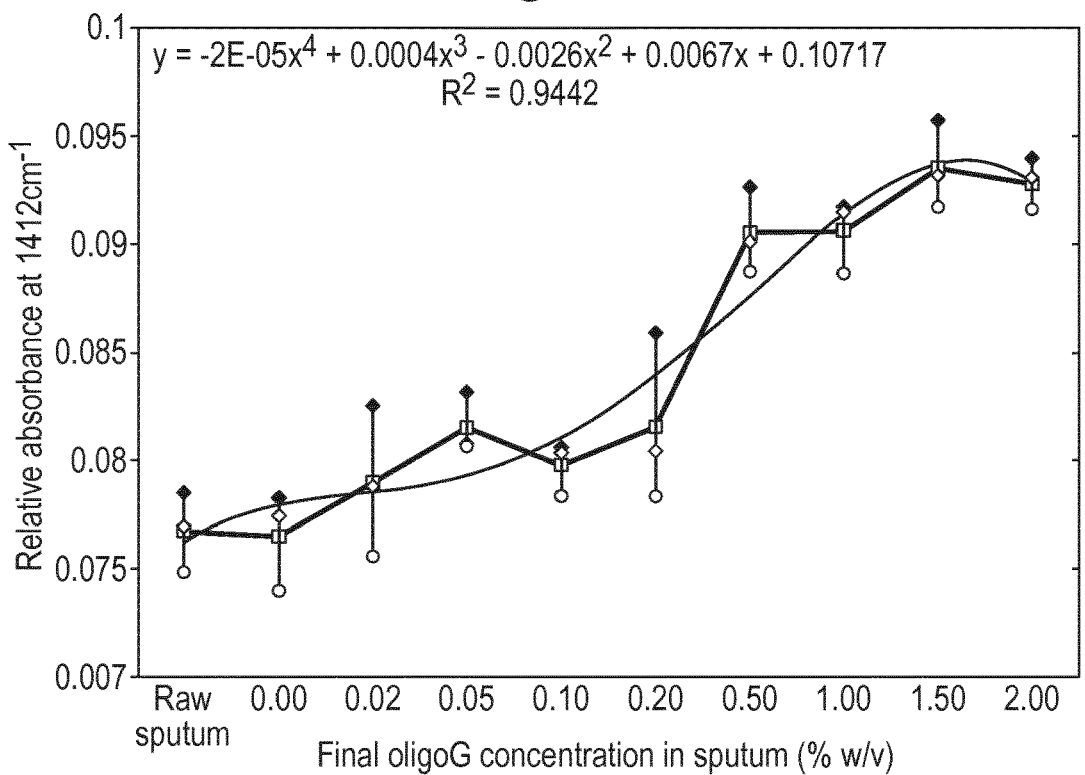
FIG. 9 shows FTIR absorbance values at 1412 $cm^{-1}$ for CF sputum samples of increasing OligoG concentration.
Figure 10:
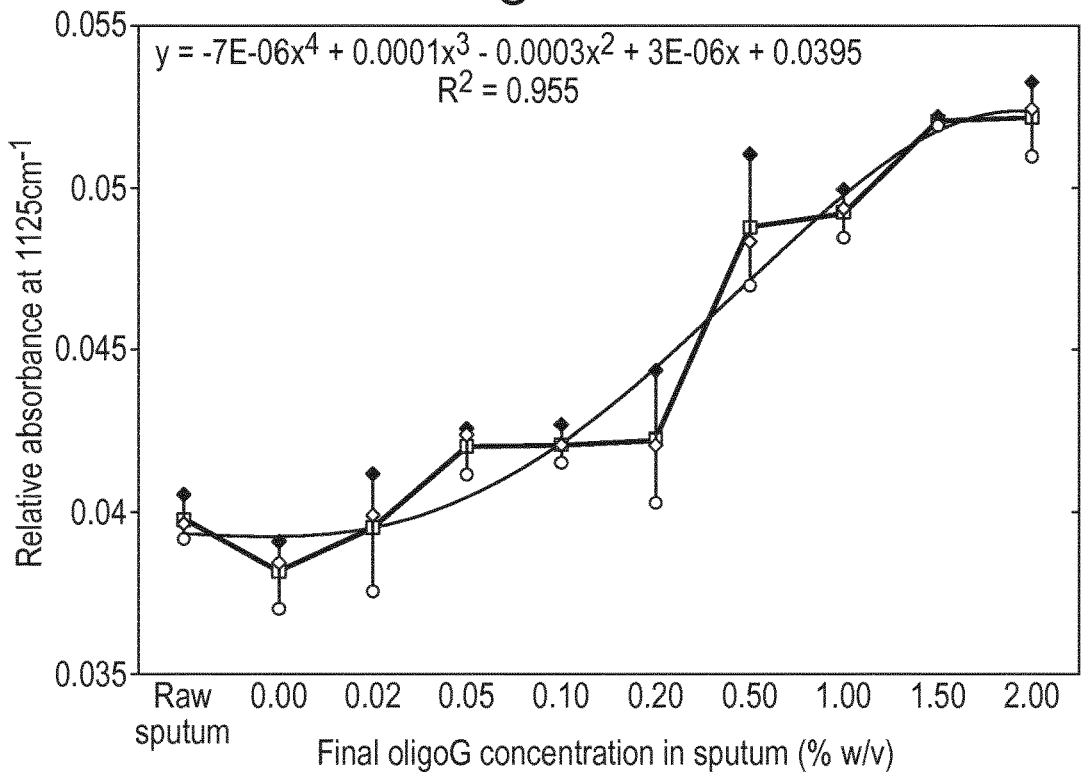
FIG. 10 shows FTIR absorbance values at 1125 $cm^{-1}$ for CF sputum samples of increasing OligoG concentration.
Figure 11:
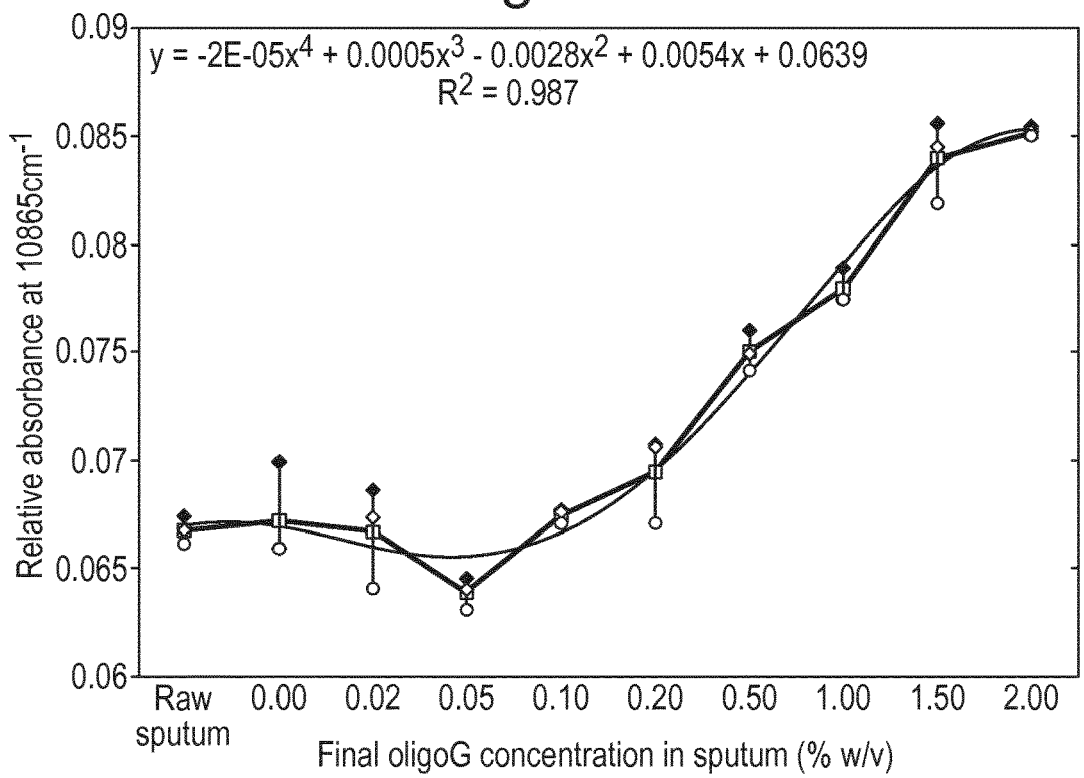
FIG. 11 shows FTIR absorbance values at 1086 $cm^{-1}$ for CF sputum samples of increasing OligoG concentration.
Figure 12:
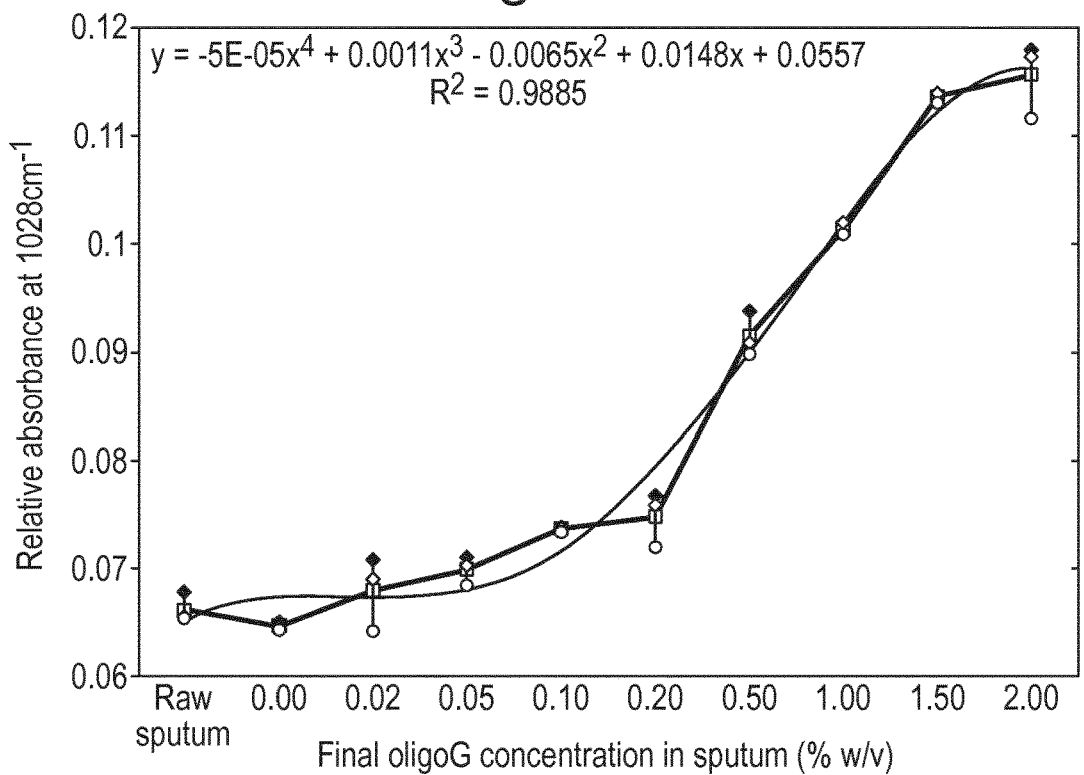
FIG. 12 shows FTIR absorbance values at 1028 $cm^{-1}$ for CF sputum samples of increasing OligoG concentration.
Figure 13:
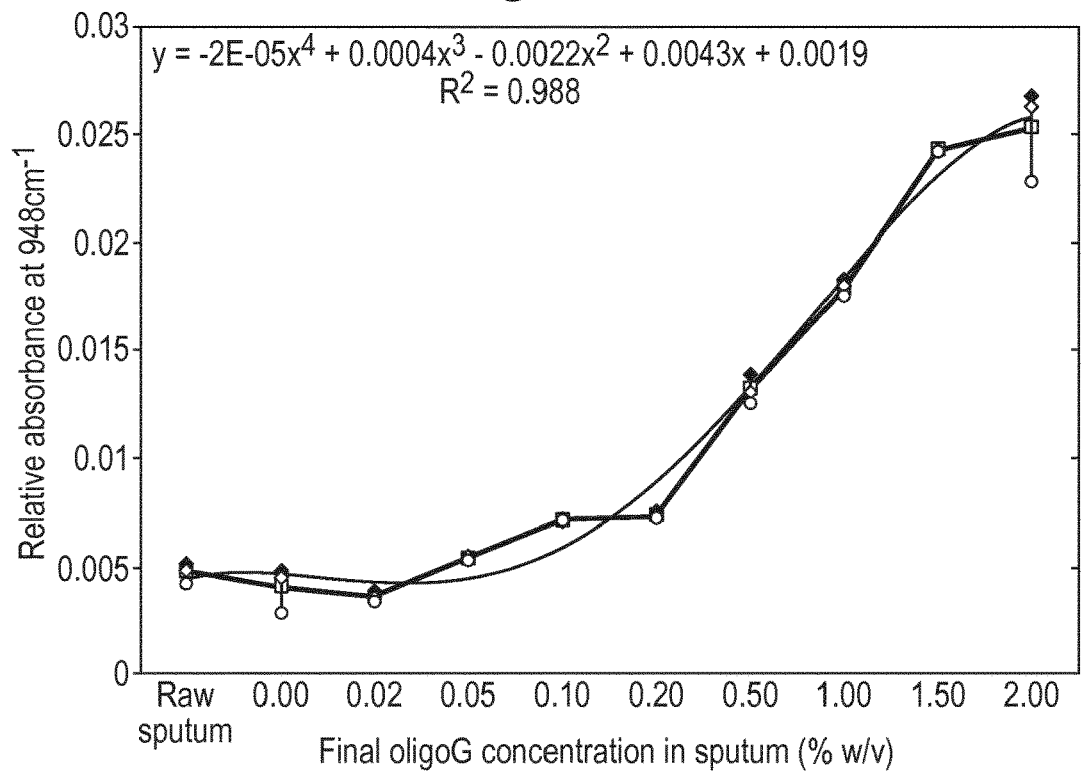
FIG. 13 shows FTIR absorbance values at 948 $cm^{-1}$ for CF sputum samples of increasing OligoG concentration.

ATR-FTIR spectroscopy has highlighted the relationship between OligoG-concentration in CF sputum and absorption by OligoG-specific IR wavenumbers. In this way, FTIR can be used to estimate the OligoG concentration in unknown CF-patient sputum samples. The IR-spectra shown in FIGS. 5, 6 and 7 demonstrate the strong affects OligoG has on sputum FTIR spectra, with increases in absorption observed across wavenumbers 1800-900 cm$^{-1}$, including the glycogen-rich region (1200-900 cm$^{-1}$), especially near wavenumbers associated with OligoG (Table 4). An increase in peaks in this region can also be observed in OligoG-incubated sputum spectra, compared to non-incubated and 0% OligoG-incubated spectra.

FIGS. 8-13 show that at each wavenumber of Table 4, the relative absorbance measured is proportional to the concentration of OligoG in the sputum sample. Thus, for sputum samples with an unknown concentration of OligoG it will be possible to measure IR absorbance at these wavenumbers and use the appropriate chart to determine the OligoG concentration in that sample.

Figure 14:
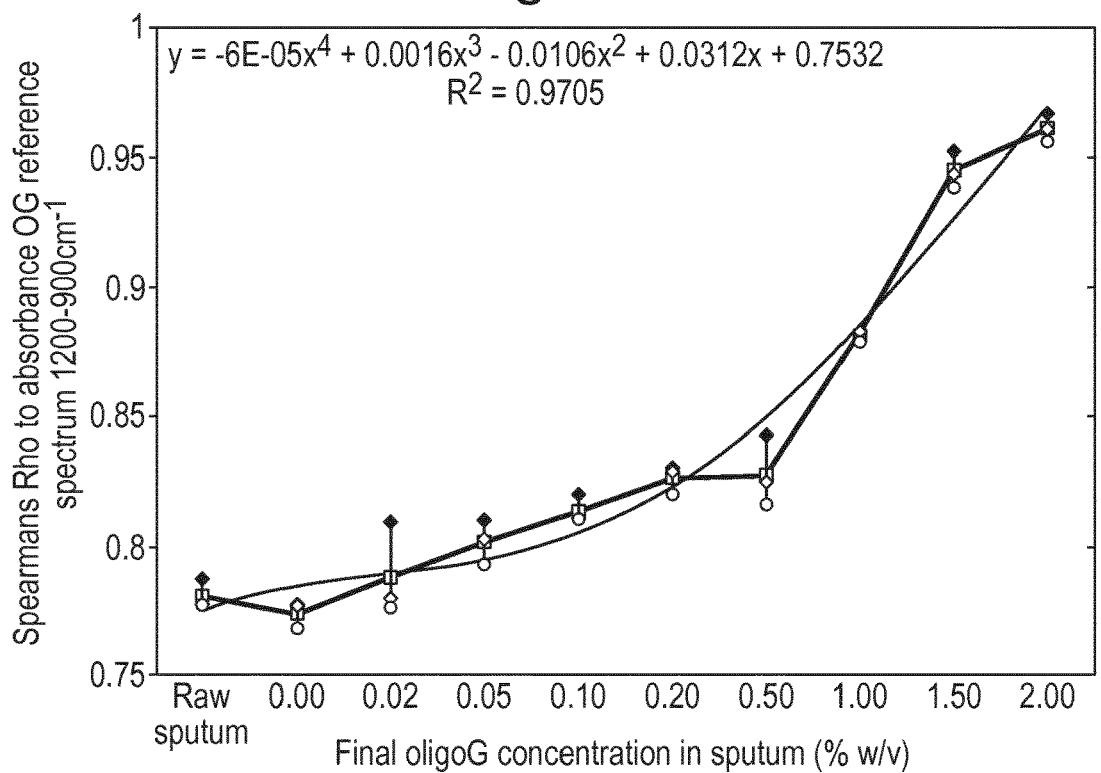
FIG. 14 shows Spearman's Rho values for correlations between the raw FTIR absorbance spectra at wavenumbers 1200-900 $cm^{-1}$ for CF sputum samples of increasing OligoG concentration and the raw FTIR absorbance spectra at wavenumbers 1200-900 $cm^{-1}$ for OligoG.
Figure 15:
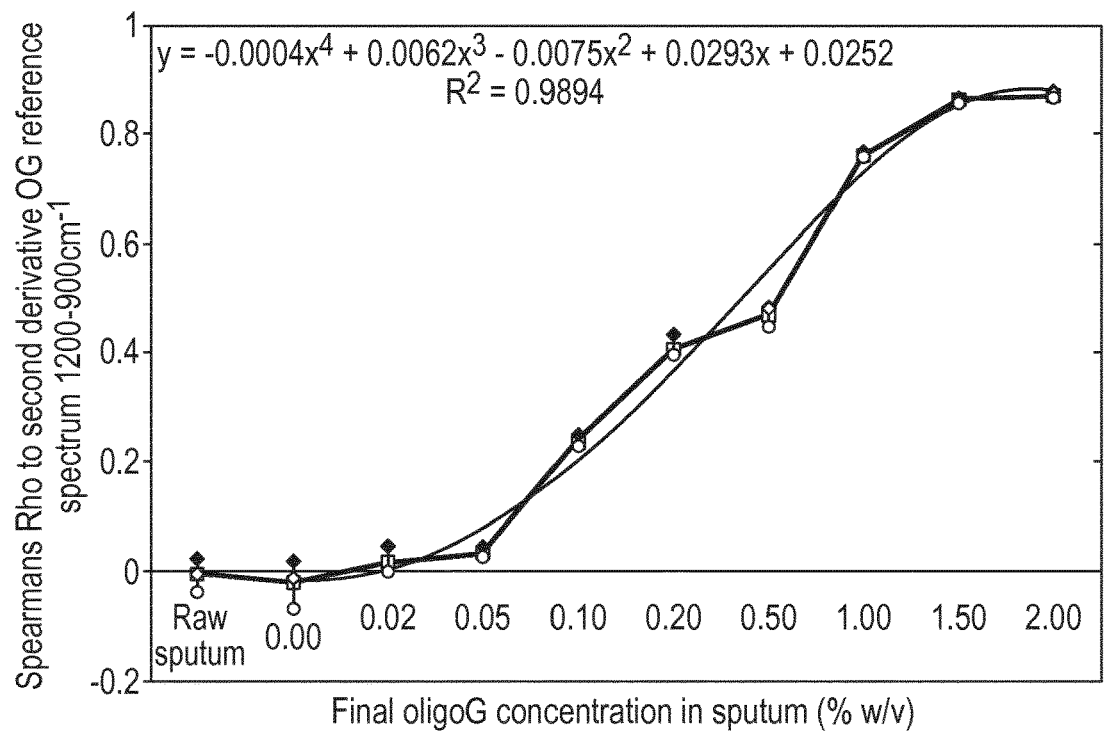
FIG. 15 shows Spearman's Rho values for correlations between the second derivative FTIR absorbance spectra at wavenumbers 1200-900 $cm^{-1}$ for CF sputum samples of increasing OligoG concentration and the second derivative FTIR absorbance spectra at wavenumbers 1200-900 $cm^{-1}$ for OligoG.

Correlation analysis of FTIR absorbance spectra in the wavenumber range 1200-900 cm$^{-1}$ shows how an increasing concentration of OligoG corresponds to an increase in Spearman's Rho coefficient when comparing the raw and second derivative sputum spectra to OligoG reference spectra (FIGS. 14 and 15). An increase in correlation can be observed even at 0.02% OligoG, which was found to be statistically significant at the 95% confidence level for both the absorbance spectra (one-tailed p=0.0142), and second derivative spectra (one-tailed p=0.0278). Correlation coefficients for all other concentrations were also found to be statistically significantly different from the non-incubated control and 0%-OligoG incubated sputum (p<0.05). The correlation coefficients for the control and 0%-OligoG incubated sputum were not found to be statistically significantly different from each other at the 95% confidence level, for either the absorbance or second derivative spectra (absorbance p=0.2261, second derivative p=0.6585), showing that the differences observed were not due to the experimental conditions.

Thus, for sputum samples with an unknown concentration of OligoG it will be possible to measure IR absorbance at these wavenumbers, correlate the raw FTIR absorbance spectra and/or the second derivative thereof with corresponding FTIR absorbance spectra from OligoG and use an appropriate standard curve to determine the OligoG concentration in that sample.

FIG. 16 further shows that when the correlation coefficients for second derivative FTIR absorbance spectra from OligoG containing sputum and second derivative FTIR absorbance spectra from OligoG are plotted over the correlation coefficients for raw FTIR absorbance spectra from OligoG containing sputum and raw FTIR absorbance spectra from OligoG, the data points cluster in distinct groups according to OligoG concentration. Thus for sputum samples with an unknown concentration of OligoG it will be possible to measure IR absorbance at these wavenumbers, correlate both the raw FTIR absorbance spectra and the second derivative thereof with corresponding FTIR absorbance spectra from OligoG and use both of the correlation coefficients so obtained to determine OligoG concentration by determining to which cluster the test data point associates in such a chart.

The invention claimed is:

1. A method for determining the concentration of alginate oligomer in a sample of body fluid, said method comprising
   (i) obtaining for the sample of body fluid one or more normalized IR absorbance values, one or more normalized IR transmittance values, one or more second derivative IR absorbance values, or one or more second derivative IR transmittance values, at one or more wavenumbers selected from one or more of the following wavenumber ranges:
      (a) 1596 cm$^{-1}$ to 1606 cm$^{-1}$,
      (b) 1407 cm$^{-1}$ to 1417 cm$^{-1}$,
      (c) 1120 cm$^{-1}$ to 1130 cm$^{-1}$,
      (d) 1081 cm$^{-1}$ to 1091 cm$^{-1}$,
      (e) 1023 cm$^{-1}$ to 1033 cm$^{-1}$, and
      (f) 943 cm$^{-1}$ to 953 cm$^{-1}$;
   (ii) for one or more of the wavenumbers selected in step (i) providing corresponding IR absorbance values, IR transmittance values, second derivative IR absorbance values, or second derivative IR transmittance values, for a plurality of samples of said body fluid which contain a range of known amounts of the alginate oligomer, and
   (iii) determining the concentration of the alginate oligomer in the sample of body fluid by determining the relative position of the values obtained in step (i) amongst the values provided in step (ii).

2. The method of claim 1, wherein:
   (i) the wavenumber range of (a) is 1597 cm$^{-1}$ to 1605 cm$^{-1}$,
   (ii) the wavenumber range of (b) is 1408 cm$^{-1}$ to 1416 cm$^{-1}$,
   (iii) the wavenumber range of (c) is 1121 cm$^{-1}$ to 1129 cm$^{-1}$,
   (iv) the wavenumber range of (d) is 1082 cm$^{-1}$ to 1090 cm$^{-1}$,
   (v) the wavenumber range of (e) is 1024 cm$^{-1}$ to 1032 cm$^{-1}$, and/or
   (vi) the wavenumber range of (f) is 944 cm$^{-1}$ to 952 cm$^{-1}$.

3. The method of claim 1, wherein the corresponding IR absorbance values, IR transmittance values, second derivative IR absorbance values, or second derivative IR transmittance values for a plurality of samples of said body fluid which contain a range of known amounts of the alginate oligomer are conveniently arranged in a tabulated form, or as a data matrix, or as Cartesian coordinates in a two dimensional Cartesian coordinate system, in which the various alginate oligomer concentrations of each of said plurality of samples of said body fluid which contain a range of known amounts of the alginate oligomer are arranged in one dimension.

4. The method of claim 3 wherein the corresponding IR absorbance values, IR transmittance values, second derivative IR absorbance values, or second derivative IR transmittance values for a plurality of samples of said body fluid which contain a range of known amounts of the alginate oligomer are provided as a standard curve in which the alginate oligomer concentrations of each of said plurality of samples of said body fluid which contain a range of known amounts of the alginate oligomer are arranged on one axis.

5. The method of claim 1, wherein one or more of the IR absorbance, IR transmittance values, second derivative IR absorbance values or second derivative IR transmittance values are provided as part of a continuous IR spectrum, or portions thereof, covering one or more of said wavenumber ranges.

6. The method of claim 1, wherein the sample is selected from the group consisting of blood, cerebrospinal fluid, faeces, gastric juice, lymph, mucus, plasma, pus, saliva, serum, semen, sweat, tears, vaginal secretion, vomit, urine and wound exudate and sputum.

7. The method of claim 1, wherein the IR absorbance or IR transmittance values or spectra are prepared by a Fourier transform infrared (FTIR) spectrometer.

8. The method of claim 1, wherein the normalized IR absorbance or IR transmittance values or spectra are normalized by Min-Max or vector normalization.

9. The method of claim 8, wherein normalization is based on absorbance or transmittance at the Amide I wavenumber.

10. The method of claim 1, wherein the sample is from a subject with an infection, bacteraemia, sepsis, septic shock; a burn, an acute wound, a chronic wound, reduced or abrogated epithelial or endothelial secretion or secretion clearance, COPD, COAD, COAP, bronchitis, cystic fibrosis, CFTR gene mutation heterozygosity, emphysema, bronchiectasis, lung cancer, asthma, pneumonia or sinusitis, a subject fitted with a medical device, a subject in need of anticoagulation therapy, or a smoker.

11. The method of claim 1, wherein the alginate oligomer has:
 (i) an average molecular weight of less than 35,000 Daltons; or
 (ii) a degree of polymerization (DP), or a number average degree of polymerization (DPn), of 4 to 100.

12. The method of claim 1, wherein the alginate oligomer has:
 (i) at least 70% G residues,
 (ii) a number average degree of polymerization in the range 5 to 20, a guluronate fraction (FG) of at least 0.85 and a mannuronate fraction (FM) of no more than 0.15; or
 (iii) at least 70% M residues.

13. An infrared spectrometer configured to perform a method as claimed in claim 1.

14. A method for determining the concentration of alginate oligomer in a sample of body fluid, said method comprising
 (a)(i) obtaining a first IR spectrum for the sample of body fluid, wherein the first IR spectrum for the sample of body fluid is a normalized IR absorbance spectrum from the wavenumber range of about 1200 $cm^{-1}$ to about 900 $cm^{-1}$ or a normalized IR transmittance spectrum from the wavenumber range of about 1200 $cm^{-1}$ to about 900 $cm^{-1}$,
 (a)(ii) providing a first IR spectrum for the alginate oligomer, wherein the first IR spectrum for the alginate oligomer is a normalized IR absorbance spectrum from the wavenumber range of about 1200 $cm^{-1}$ to about 900 $cm^{-1}$ when the first spectrum for the sample of body fluid is an absorbance spectrum, or a normalized IR transmittance spectrum from the wavenumber range of about 1200 $cm^{-1}$ to about 900 $cm^{-1}$ when the first IR spectrum for the sample of body fluid is a transmittance spectrum,
 (a)(iii) performing a non-parametric correlation analysis on the first IR spectrum for the sample of body fluid and the first IR spectrum for the alginate oligomer thereby producing a first correlation coefficient,
 (a)(iv) providing corresponding correlation coefficients for a plurality of samples of said body fluid which contain a range of known amounts of the alginate oligomer, and
 (a)(v) determining the concentration of the alginate oligomer in the sample of body fluid by determining the relative position of the first correlation coefficient obtained in step (a)(iii) amongst the correlation coefficients of step (a)(iv); or
 (b)(i) obtaining a second IR spectrum for the sample of body fluid, wherein the second IR spectrum for the sample of body fluid is the second derivative of an IR absorbance spectrum from the wavenumber range of about 1200 $cm^{-1}$ to about 900 $cm^{-1}$ or the second derivative of an IR transmittance spectrum from the wavenumber range of about 1200 $cm^{-1}$ to about 900 $cm^{-1}$,
 (b)(ii) providing a second IR spectrum for the alginate oligomer, wherein the second IR spectrum for the alginate oligomer is the second derivative of an IR absorbance spectrum from the wavenumber range of about 1200 $cm^{-1}$ to about 900 $cm^{-1}$ when the second spectrum for the sample of body fluid is an absorbance spectrum, or the second derivative of an IR transmittance spectrum from the wavenumber range of about 1200 $cm^{-1}$ to about 900 $cm^{-1}$ when the second spectrum for the sample of body fluid is a transmittance spectrum,
 (b)(iii) performing a non-parametric correlation analysis on the second IR spectrum for the sample of body fluid and the second IR spectrum for the alginate oligomer thereby producing a second correlation coefficient,
 (b)(iv) providing corresponding correlation coefficients for a plurality of samples of said body fluid which contain a range of known amounts of the alginate oligomer, and
 (b)(v) determining the concentration of the alginate oligomer in the sample of body fluid by determining the relative position of the second correlation coefficient obtained in step (b)(iii) amongst the correlation coefficients of step (b)(iv).

15. The method of claim 14, wherein the corresponding correlation coefficients of step (a)(iv) or (b)(iv) are arranged in a tabulated form, as a data matrix, or as Cartesian coordinates in a two dimensional Cartesian coordinate system, in which the alginate oligomer concentrations of each of said plurality of samples of said body fluid which contain a range of known amounts of the alginate oligomer are arranged in one dimension.

16. The method of claim 15 wherein the corresponding correlation coefficients of step (a)(iv) or (b)(iv) are provided as a standard curve in which the alginate oligomer concentrations of each of said plurality of samples of said body fluid which contain a range of known amounts of the alginate oligomer are arranged on one axis.

17. The method of claim 14, wherein the non-parametric correlation analysis is Spearman's Rank, Kendall's Tau and/or point biserial correlation analysis.

18. A method for determining the concentration of alginate oligomer in a sample of body fluid, said method comprising
    (i) obtaining an first IR spectrum for the sample of body fluid, wherein the first IR spectrum for the sample of body fluid is a normalized IR absorbance spectrum from the wavenumber range of about 1200 cm$^{-1}$ to about 900 cm$^{-1}$ or a normalized IR transmittance spectrum from the wavenumber range of about 1200 cm$^{-1}$ to about 900 cm$^{-1}$,
    (ii) obtaining a second IR spectrum for the sample of body fluid, wherein the second IR spectrum for the sample of body fluid is the second derivative of an IR absorbance spectrum from the wavenumber range of about 1200 cm$^{-1}$ to about 900 cm$^{-1}$ or the second derivative of an IR transmittance spectrum from the wavenumber range of about 1200 cm$^{-1}$ to about 900 cm$^{-1}$,
    (iii) providing a first IR spectrum for the alginate oligomer, wherein the first IR spectrum for the alginate oligomer is a normalized IR absorbance spectrum from the wavenumber range of about 1200 cm$^{-1}$ to about 900 cm$^{-1}$ when the first IR spectrum for the sample of body fluid is an absorbance spectrum, or a normalized IR transmittance spectrum from the wavenumber range of about 1200 cm$^{-1}$ to about 900 cm$^{-1}$ when the first IR spectrum for the sample of body fluid is a transmittance spectrum,
    (iv) providing a second IR spectrum for the alginate oligomer, wherein the second IR spectrum for the alginate oligomer is the second derivative of an IR absorbance spectrum from the wavenumber range of about 1200 cm$^{-1}$ to about 900 cm$^{-1}$ when the second IR spectrum for the sample of body fluid is an IR absorbance spectrum, or the second derivative of an IR transmittance spectrum from the wavenumber range of about 1200 cm$^{-1}$ to about 900 cm$^{-1}$ when the second IR spectrum for the sample of body fluid is an IR transmittance spectrum,
    (v) performing a non-parametric correlation analysis on the first IR spectrum for the sample of body fluid and the first IR spectrum for the alginate oligomer thereby producing a first correlation coefficient,
    (vi) performing a non-parametric correlation analysis on the second IR spectrum for the sample of body fluid and the second IR spectrum for the alginate oligomer thereby producing a second correlation coefficient,
    (vii) providing corresponding first correlation coefficients and second correlation coefficients for a plurality of samples of said body fluid which contain a range of known concentrations of the alginate oligomer as Cartesian coordinates in a two or three dimensional Cartesian coordinate system, and
    (viii) determining the concentration of the alginate oligomer in the sample of body fluid by determining the relative position of a Cartesian coordinate comprising the first and second correlation coefficients obtained in steps (v) and (vi) in the Cartesian coordinate system of step (vii).

19. A method for determining the presence or absence of an alginate oligomer in a sample of body fluid, said method comprising
    (i) obtaining an first IR spectrum for the sample of body fluid, wherein the first IR spectrum for the sample of body fluid is a normalized IR absorbance spectrum from the wavenumber range of about 1200 cm$^{-1}$ to about 900 cm$^{-1}$ or a normalized IR transmittance spectrum from the wavenumber range of about 1200 cm$^{-1}$ to about 900 cm$^{-1}$,
    (ii) obtaining a second IR spectrum for the sample of body fluid, wherein the second IR spectrum for the sample of body fluid is the second derivative of an IR absorbance spectrum from the wavenumber range of about 1200 cm$^{-1}$ to about 900 cm$^{-1}$ or the second derivative of an IR transmittance spectrum from the wavenumber range of about 1200 cm$^{-1}$ to about 900 cm$^{-1}$,
    (iii) providing a first IR spectrum for the alginate oligomer, wherein the first IR spectrum for the alginate oligomer is a normalized IR absorbance spectrum from the wavenumber range of about 1200 cm$^{-1}$ to about 900 cm$^{-1}$ when the first spectrum for the sample of body fluid is an absorbance spectrum, or a normalized IR transmittance spectrum from the wavenumber range of about 1200 cm$^{-1}$ to about 900 cm$^{-1}$ when the first IR spectrum for the sample of body fluid is a transmittance spectrum,
    (iv) providing a second IR spectrum for the alginate oligomer, wherein the second IR spectrum for the alginate oligomer is the second derivative of an IR absorbance spectrum from the wavenumber range of about 1200 cm$^{-1}$ to about 900 cm$^{-1}$ when the second spectrum for the sample of body fluid is an absorbance spectrum, or the second derivative of an IR transmittance spectrum from the wavenumber range of about 1200 cm$^{-1}$ to about 900 cm$^{-1}$ when the second spectrum for the sample of body fluid is a transmittance spectrum,
    (v) performing a non-parametric correlation analysis on the first IR spectrum for the sample of body fluid and the first IR spectrum for the alginate oligomer thereby producing a first correlation coefficient,
    (vi) performing a non-parametric correlation analysis on the second IR spectrum for the sample of body fluid and the second IR spectrum for the alginate oligomer thereby producing a second correlation coefficient,
    (vii) providing corresponding first correlation coefficients and second correlation coefficients for a plurality of samples of said body fluid which contain an alginate oligomer and corresponding first correlation coefficients and second correlation coefficients for a plurality of samples of said body fluid which do not contain an alginate oligomer as Cartesian coordinates in a two or three dimensional Cartesian coordinate system, and
    (viii) determining the presence or absence of an alginate oligomer in the sample of body fluid by determining the relative position of a Cartesian coordinate comprising the first and second correlation coefficients obtained in steps (v) and (vi) in the Cartesian coordinate system of step (vii), wherein
        (a) collocation of said Cartesian coordinate comprising the first and second correlation coefficients obtained in steps (v) and (vi) with the Cartesian coordinates of the samples of said body fluid which do not contain an alginate oligomer is indicative that the sample does not contain an alginate oligomer, and
        (b) collocation of said Cartesian coordinate comprising the first and second correlation coefficients obtained in steps (v) and (vi) with the Cartesian coordinates of the samples of said body fluid which do contain an alginate oligomer is indicative that the sample does contain an alginate oligomer.

20. The method for determining the presence or absence of an alginate oligomer in a sample of body fluid of claim 19, said method comprising:
   (i) obtaining an first IR spectrum for the sample of body fluid, wherein the first IR spectrum for the sample of body fluid is a normalized IR absorbance spectrum from the wavenumber range of about 1200 cm$^{-1}$ to about 900 cm$^{-1}$ or a normalized IR transmittance spectrum from the wavenumber range of about 1200 cm$^{-1}$ to about 900 cm$^{-1}$,
   (ii) obtaining a second IR spectrum for the sample of body fluid, wherein the second IR spectrum for the sample of body fluid is the second derivative of an IR absorbance spectrum from the wavenumber range of about 1200 cm$^{-1}$ to about 900 cm$^{-1}$ or the second derivative of an IR transmittance spectrum from the wavenumber range of about 1200 cm$^{-1}$ to about 900 cm$^{-1}$,
   (iii) providing a first IR spectrum for the alginate oligomer, wherein the first IR spectrum for the alginate oligomer is a normalized IR absorbance spectrum from the wavenumber range of about 1200 cm$^{-1}$ to about 900 cm$^{-1}$ when the first spectrum for the sample of body fluid is an absorbance spectrum, or a normalized IR transmittance spectrum from the wavenumber range of about 1200 cm$^{-1}$ to about 900 cm$^{-1}$ when the first IR spectrum for the sample of body fluid is a transmittance spectrum,
   (iv) providing a second IR spectrum for the alginate oligomer, wherein the second IR spectrum for the alginate oligomer is the second derivative of an IR absorbance spectrum from the wavenumber range of about 1200 cm$^{-1}$ to about 900 cm$^{-1}$ when the second spectrum for the sample of body fluid is an IR absorbance spectrum, or the second derivative of an IR transmittance spectrum from the wavenumber range of about 1200 cm$^{-1}$ to about 900 cm$^{-1}$ when the second spectrum for the sample of body fluid is a transmittance spectrum,
   (v) performing a non-parametric correlation analysis on the first IR spectrum for the sample of body fluid and the first IR spectrum for the alginate oligomer thereby producing a first correlation coefficient,
   (vi) performing a non-parametric correlation analysis on the second IR spectrum for the sample of body fluid and the second IR spectrum for the alginate oligomer thereby producing a second correlation coefficient,
   (vii) inputting the first correlation coefficient of step (v) into the linear prediction model Formula I $$Y=nX+m \qquad \text{Formula I}$$

as X and determining a value for Y,
   (viii) wherein a value for Y which is equal to or less than the second correlation coefficient of step (vi) is an indication that the alginate oligomer is present in the sample of body fluid, and a value for Y which is greater than the second correlation coefficient of step (vi) is an indication that the alginate oligomer is absent from the sample of body fluid, and wherein the linear regression model and has been prepared by
      (a) obtaining one or more normalized IR absorbance spectra or one or more IR transmittance spectra from the wavenumber range of about 1200 cm$^{-1}$ to about 900 cm$^{-1}$ for a plurality of samples of said body fluid which contain the alginate oligomer and a plurality of samples of said body fluid which do not contain the alginate oligomer,
      (b) providing a normalized IR absorbance spectrum from the wavenumber range of about 1200 cm$^{-1}$ to about 900 cm$^{-1}$ for the alginate oligomer when the spectra of step (a) are IR absorbance spectra, or a normalized IR transmittance spectrum from the wavenumber range of about 1200 cm$^{-1}$ to about 900 cm$^{-1}$ for the alginate oligomer when the spectra of step (a) are IR transmittance spectra,
      (c) performing a non-parametric correlation analysis on the IR spectra of step (a) and the IR spectrum for the alginate oligomer of step (b) thereby producing at least one correlation coefficient for each of the samples of step (a); and
      (d) obtaining the second derivatives of one or more IR absorbance spectra or the second derivatives of one or more IR transmittance spectra from the wavenumber range of about 1200 cm$^{-1}$ to about 900 cm$^{-1}$ for the plurality of samples of said body fluid which contain the alginate oligomer and the plurality of samples of said body fluid which do not contain the alginate oligomer of step (a),
      (e) providing the second derivative of a normalized IR absorbance spectrum from the wavenumber range of about 1200 cm$^{-1}$ to about 900 cm$^{-1}$ for the alginate oligomer when the spectra of step (d) are the second derivatives of IR absorbance spectra, or the second derivative of a normalized IR transmittance spectrum from the wavenumber range of about 1200 cm$^{-1}$ to about 900 cm$^{-1}$ for the alginate oligomer when the spectra of step (d) are the second derivatives of IR transmittance spectra,
      (f) performing a non-parametric correlation analysis on the second derivatives of the IR spectra of step (d) and the second derivative of the IR spectrum for the alginate oligomer of step (e) thereby producing at least one further correlation coefficient for each of the samples of step (a); and
      (g) for each of the plurality of samples of step (a) plotting the further correlation coefficient produced in step (f) and the correlation coefficient produced in step (c) as a Cartesian coordinates in a two dimensional Cartesian coordinate system, and
      (h) determining the optimum separation of the Cartesian coordinates of the plurality of samples of said body fluid which contain the alginate oligomer and the Cartesian coordinates of the plurality of samples of said body fluid which do not contain the alginate oligomer to yield a separation threshold defined by the linear regression model Y=nX+m, wherein n and m are numerical constants, and X is a correlation coefficient of step (c) for a sample of step (a).

21. A method for determining the presence or absence of an alginate oligomer in a sample of body fluid, said method comprising:
   (i) obtaining an infrared (IR) spectrum for the sample of body fluid, wherein the IR spectrum for the sample of body fluid is the second derivative of an IR absorbance spectrum from the wavenumber range of about 1200 cm$^{-1}$ to about 900 cm$^{-1}$ or the second derivative of an IR transmittance spectrum from the wavenumber range of about 1200 cm$^{-1}$ to about 900 cm$^{-1}$,
   (ii) providing an IR spectrum for the alginate oligomer, wherein the IR spectrum for the alginate oligomer is the second derivative of an IR absorbance spectrum from the wavenumber range of about 1200 cm$^{-1}$ to about 900

$cm^{-1}$ when the IR spectrum for the sample of body fluid is an absorbance spectrum, or a second derivative IR transmittance spectrum from the wavenumber range of about 1200 $cm^{-1}$ to about 900 $cm^{-1}$ when the IR spectrum for the sample of body fluid is a transmittance spectrum, and (iii) comparing the IR spectrum for the sample of body fluid to the IR spectrum for the alginate oligomer, wherein (a) an IR spectrum for the sample of body fluid which corresponds to the IR spectrum for the alginate oligomer is an indication that the alginate oligomer is present in the sample of body fluid, and (b) an IR spectrum for the sample of body fluid which does not correspond to the IR spectrum for the alginate oligomer is an indication that the alginate oligomer is absent from the sample of body fluid.

\* \* \* \* \*